(12) United States Patent
Kawamura et al.

(10) Patent No.: US 8,276,581 B2
(45) Date of Patent: Oct. 2, 2012

(54) PREFILLED TYPE NASAL DRIP APPLIANCE

(75) Inventors: Hideaki Kawamura, Tokyo (JP); Hiroshi Togashi, Tokyo (JP)

(73) Assignee: Daikyo Seiko, Ltd., Tokyo (JP)

( * ) Notice: Subject to any disclaimer, the term of this patent is extended or adjusted under 35 U.S.C. 154(b) by 354 days.

(21) Appl. No.: 12/740,067

(22) PCT Filed: Oct. 28, 2008

(86) PCT No.: PCT/JP2008/069495
§ 371 (c)(1),
(2), (4) Date: Apr. 27, 2010

(87) PCT Pub. No.: WO2009/057572
PCT Pub. Date: May 7, 2009

(65) Prior Publication Data
US 2010/0258115 A1    Oct. 14, 2010

(30) Foreign Application Priority Data

Oct. 30, 2007    (JP) .................................. 2007-281437

(51) Int. Cl.
*A61M 11/00* (2006.01)
(52) U.S. Cl. .......... 128/200.22; 128/200.14; 128/207.18
(58) Field of Classification Search ............. 128/200.22, 128/200.14, 207.18; 239/329, 533.1; 222/129; 604/218, 239
See application file for complete search history.

(56) References Cited

U.S. PATENT DOCUMENTS

| | | | |
|---|---|---|---|
| 5,961,489 A | 10/1999 | Hirota | |
| 7,182,277 B2 * | 2/2007 | Vedrine et al. | ................ 239/329 |
| 7,481,797 B2 | 1/2009 | Mahurkar | |
| 2002/0174864 A1 | 11/2002 | Alchas | |
| 2003/0032928 A1 | 2/2003 | Sudo et al. | |
| 2003/0075168 A2 | 4/2003 | Alchas | |

FOREIGN PATENT DOCUMENTS

| | | |
|---|---|---|
| JP | 8010325 A | 1/1996 |
| JP | 9299484 A | 11/1997 |
| JP | 3047521 U | 1/1998 |
| JP | 11114065 A | 4/1999 |
| JP | 2001137344 A | 5/2001 |
| JP | 2003164524 A | 6/2003 |
| JP | 2006271940 A | 10/2006 |
| JP | 2007054621 A | 3/2007 |
| JP | 3136169 U | 9/2007 |
| WO | 0164266 A1 | 9/2001 |

* cited by examiner

Primary Examiner — Steven Douglas
(74) Attorney, Agent, or Firm — The Webb Law Firm

(57) ABSTRACT

Provided is an easy-to-handle prefilled type nasal drip appliance which can spray medical solution surely into the nostril while holding down the production cost. A syringe barrel has a spray hole and a latching portion of a center stopper on one side, with a conduction portion of medical solution being provided at the latching portion, and has a portion protruding inward of the inner circumferential surface formed on the other end side. A plunger has a portion protruding outward of the outer circumferential surface formed substantially in the axial center wherein both protrusions engage with each other. When the plunger is moved in the spray direction of the syringe barrel to get over the plunger side protrusion and disengaged, the medical solution moves the center stopper in the spray direction to form a medical solution inflow groove between the conduction portion formed at the center stopper latching portion and the center stopper. Consequently, a medical solution storage portion and the spray hole are interconnected and the medical solution can be sprayed.

16 Claims, 18 Drawing Sheets

Prior Art

Prior Art

Prior Art

PREFILLED TYPE NASAL DRIP APPLIANCE

TECHNICAL FIELD

The present invention relates to a nasal drip appliance for a medical drug and a medical treatment. More specifically, the present invention relates to a prefilled type nasal drip appliance in which a medicinal solution is stored and retained in a syringe barrel in advance and the medicinal solution can be sprayed into the nostril with rapidity as needed.

BACKGROUND ART

A wide variety of nasal drip appliances have been used in order to carry out a nasal drip of a predetermined medicinal solution into the nostril. Such a nasal drip appliance is disclosed in the Patent literature document 1 for instance. As shown in FIG. 14, a medicinal solution 106 is filled between a syringe barrel 102 and a plunger 104, and a nasal drop appliance 100 is inserted into the nostril. In this state, the plunger 104 is moved in a direction of an axis of the syringe barrel 102, whereby the medicinal solution 106 is sprayed from a plurality of spray holes 108 that have been formed on the leading end of the syringe barrel 102 to the nostril.

As shown in FIG. 15, the Patent document 2 discloses a nasal drip appliance 200 in which a medicinal solution 206 is filled between a syringe barrel 202 and a plunger 204, and a through hole for the medicinal solution 206 is formed in the leading end of the syringe barrel 202. In addition, a skirt valve 212 and an adapter 214 provided with a spray hole 208 of the medicinal solution 206 are attached to the leading end side of the syringe barrel 202. Moreover, a stopper 216 is fitted into the space between the rear end of the syringe barrel 202 and the rear end of the plunger 204.

For the nasal drip appliance 200, the medicinal solution 206 can be sprayed outward from the spray hole 208 of the adapter 214 only during a nasal drip of a medicinal solution. A movement distance of the plunger 204 can be limited by the stopper 216, whereby an amount of a spray of the medicinal solution 206 can be adjusted.

As shown in FIG. 16, the Patent document 3 discloses a nasal drip appliance 300 in which an adapter 314 provided with two spray nozzles 318 and 320 that can be inserted into two nostrils is attached to the leading end side of the syringe barrel 302 of the nasal drip appliance 300. By this configuration, a medicinal solution 306 can be sprayed into the both nostrils in one fell swoop.

On the other hand, as shown in FIG. 17 for instance, the Patent document 4 discloses a nasal drip appliance 400 of a so-called prefilled type in which a medicinal solution 406 has been stored and retained between a syringe barrel 402 and a plunger 404 before a usage. The prefilled type nasal drip appliance can be used as quick as possible when being used.

The prefilled type nasal drip appliance 400 can be used as quick as possible when being used. In addition, it is not necessary to carry out a filling operation of the medicinal solution 406 into a nasal drip appliance. Consequently, a mistake of a kind or an amount of the medicinal solution 406 can be prevented from occurring even in the event of an emergency, and a microbial contamination can also be prevented, thus improving a sanitarian level advantageously. As a result, the prefilled type nasal drip appliance 400 has been preferably used in recent years from an aspect of an efficiency of a medical treatment in a medical treatment site and an aspect of a prevention of a bacterial contamination.

The Patent document 5 discloses a nasal drip appliance 500 that has the following configuration. As shown in FIG. 18(a), only a gasket part 504a is removed from a plunger 504, and a medicinal solution 506 is stored and retained between a syringe barrel 502 and the gasket part 504a in advance. As shown in FIG. 18(b), a shaft part 504b of the plunger 504 is attached to the gasket part 504a during a usage, and an adapter 514 provided with a valve 512 is attached to the leading end side of the syringe barrel 502, whereby the nasal drip appliance 500 can be used.

A conventional nasal drip appliance and a conventional prefilled type nasal drip appliance that have the above described configurations enable a predetermined medicinal solution to be sprayed into the nostril.

Patent document 1: Japanese Patent Application Laid-Open Publication No. 2006-271940
Patent document 2: Japanese Patent Application Laid-Open Publication No. 2001-137344
Patent document 3: Japanese Patent Application Laid-Open Publication No. 11-114065
Patent document 4: Japanese Patent Application Laid-Open Publication No. 09-299484
Patent document 5: Japanese Registered Utility Model No. 3047521

However, for the nasal drip appliance 100 that is disclosed in the Patent document 1, immediately after a medicinal solution 106 is filled between a syringe barrel 102 and a plunger 104, the medicinal solution 106 leaks from the spray holes 108 that have been formed on the leading end of the syringe barrel 102 in some cases. Moreover, in the case in which the plunger 104 is moved slowly in a direction of an axis of the syringe barrel 102, the medicinal solution 106 slowly leaks from the spray holes 108, whereby the medicinal solution 106 cannot be in the form of a liquid mist. Consequently, the medicinal solution cannot be sprayed into the nostril in some cases.

The nasal drip appliance 200 that is disclosed in the Patent document 2 has a large number of components, and a production cost thereof is increased. Moreover, when the plunger 204 is moved in a direction of an axis of the syringe barrel 202, the valve does not function in the case in which a pressure of a certain level or more is not applied to the skirt valve 212. Furthermore, the medicinal solution 206 leaks from the spray hole 208, whereby the medicinal solution 206 cannot be in the form of a liquid mist. As a result, the medicinal solution 206 in the form of a liquid mist cannot be sprayed into the nostril in some cases.

The nasal drip appliance 300 that is disclosed in the Patent document 3 is an appliance that sprays the medicinal solution 306 into the both nostrils at one time. Consequently, the nasal drip appliance 300 cannot be used in the case in which a medicinal solution is sprayed into only a nostril on one side, and a use application is restricted. Moreover, the nasal drip appliance 300 is large in size, whereby portability thereof is deteriorated and a production cost thereof is increased.

The nasal drip appliances 400 and 500 that are disclosed in the Patent documents 4 and 5, respectively, have a large number of components, and a production cost thereof is increased. Moreover, when the plunger 404 or 504 is moved in a direction of an axis of the syringe barrel 402 or 502, the medicinal solution 406 or 506 cannot be in the form of a liquid mist in the case in which a pressure of a certain level or more is not applied to the plunger 404 or 504. As a result, the medicinal solution 406 or 506 in the form of a liquid mist cannot be sprayed into the nostril in some cases.

Moreover, the nasal drip appliance that is disclosed in the Patent document 2 or 3 can also be applied to a prefilled type nasal drip appliance. However, even in this case, the problems that have been described above cannot be solved.

As described above, a conventional nasal drip appliance and a conventional prefilled type nasal drip appliance have the problems that have been described above. In the case in which a medicinal solution is to be sprayed, it is determined whether or not a medicinal solution is sprayed with a certainty depending on the level of a power force of a person that handles a nasal drip appliance. Consequently, in the case in which a nasal drip appliance is handled, all people cannot always spray a medicinal solution into the nostril with a certainty in the same way.

The present invention was made in consideration of such conditions, and an attention is focused on a prefilled type nasal drip appliance among the nasal drip appliances. An object of the present invention is to provide a prefilled type nasal drip appliance that enables a production cost thereof to be suppressed, that can be handled by all people in the same way, that can be easily handled, and that enables a medicinal solution to be sprayed into the nostril with a certainty.

SUMMARY OF THE INVENTION

The present invention was made in order to solve the above problems of the conventional art.

A prefilled type nasal drip appliance in accordance with the present invention is characterized by comprising:
a syringe barrel provided with a spray hole of a medicinal solution on one side and a medical solution storage part that stores the medicinal solution in advance on the other side;
an elastic piston that is inserted into the syringe barrel in a slidable manner to the inner circumferential face of the syringe barrel;
a plunger that is attached to the rear end of the piston and that enables the piston to be moved in a direction of an axis of the syringe barrel; and
an elastic center stopper that is inserted into the syringe barrel in such a manner that the center stopper is located between the spray hole and the piston and that can slide on the inner circumferential face of the syringe barrel,
wherein the medicinal solution is stored between the center stopper and the piston in a liquid-tight state in advance,
the syringe barrel is provided with a center stopper locking part between the spray hole formed on one side and the center stopper, a conduction part that is a passage way that can introduce the medicinal solution is formed at one location or a plurality of locations in the center stopper locking part,
a syringe barrel side protruding part that is protruded inside from the inner circumferential face of the syringe barrel is formed on the other end side of the syringe barrel,
the plunger is provided with a plunger side protruding part that is protruded outside from the outer circumferential face of the plunger is formed at a generally central part in a direction of an axis of the plunger,
the syringe barrel side protruding part and the plunger side protruding part are configured to be engaged with each other and the engagement is configured to be released with a pressure of a predetermined level or more when the plunger is moved in a direction of the spray hole of the syringe barrel and the plunger side protruding part gets over the syringe barrel side protruding part,
a pressure of a predetermined level or more is applied to the plunger, the plunger is moved in a direction of the spray hole of the syringe barrel, the engagement of the plunger side protruding part and the syringe barrel side protruding part is released,
the medicinal solution moves the center stopper in a direction of the spray hole by the pressure that is applied to the plunger in the release of the engagement,
the center stopper gets over the conduction part that is formed to the center stopper locking part, a medical solution inflow groove is formed between the conduction part and the center stopper, the medical solution storage part and the spray hole are interconnected with each other, and
the medicinal solution is therefore flown and moved in a direction of the spray hole from the medical solution inflow groove, whereby the medicinal solution can be sprayed from the spray hole.

By the above configuration, in the case in which the plunger is moved in a direction of an axis of the syringe barrel, the syringe barrel side protruding part of the syringe barrel gets over the plunger side protruding part of the plunger. At that time, a pressure of a predetermined level is applied to the syringe barrel.

By the above configuration, a pressure of a predetermined level can be ensured, and the center stopper gets over the conduction part, whereby the medicinal solution is moved through the medical solution inflow groove to the side of the spray hole. Consequently, the medicinal solution can be sprayed from the spray hole. As a result, everyone can spray the medicinal solution into the nostril at any time with a certainty.

Moreover, for the above configuration, only the conduction part and the syringe barrel side protruding part are formed on the side of the inner circumferential face of the syringe barrel, and only the plunger side protruding part is formed on the side of the outer circumferential face of the plunger. Consequently, a number of components can be reduced and a production cost can be suppressed as compared with a conventional configuration.

The prefilled type nasal drip appliance in accordance with the present invention is characterized in that the conduction part that is formed to the center stopper locking part is formed in the range at least equivalent to a thickness width in a direction of an axis of the center stopper that is moved in a direction of an axis of the syringe barrel or in the range equivalent to or larger than a width of a contact part of the center stopper that comes into contact with the syringe barrel.

By forming the conduction part in the above range, in the case in which the center stopper gets over the conduction part, the medical solution inflow groove can be formed with a certainty. Consequently, the medicinal solution is flown and moved on the side of the spray hole, whereby the medical solution can be sprayed from the spray hole into the nostril.

The prefilled type nasal drip appliance in accordance with the present invention is characterized in that the plunger side protruding part that is formed on the plunger is formed at one location or a plurality of locations in a direction of an axis of the plunger.

By the above configuration, a movement distance of the plunger that is moved in a direction of an axis of the syringe barrel can be adjusted at the forming location of the plunger side protruding part, whereby an amount of a spray of the medicinal solution can be adjusted. Consequently, in the case in which the medicinal solution of an amount that enables the sprays of a plurality of times is stored into the medical solution storage part and the plunger side protruding parts of the number of the sprays are formed at a predetermined interval in a direction of an axis of the plunger, the plunger side protruding part gets over the syringe barrel side protruding part a plurality of times. As a result, the medicinal solution of an amount for once can be sprayed for every time with a certainty.

The prefilled type nasal drip appliance in accordance with the present invention is characterized in that:

the plunger side protruding part that is formed on the plunger is formed at a plurality of locations in a direction of an axis of the plunger, the syringe barrel is provided with the plunger stopper part that includes; a plunger stopper that is protruded inside from the inner circumferential face of the syringe barrel and that stops a movement of the plunger in a direction of an axis of the syringe barrel in the case in which the plunger side protruding part is abutted to the plunger stopper; and a cut part that is formed on an inner circumference the same as that of the plunger stopper and that enables the plunger side protruding part to pass through the cut part, and the plunger side protruding part and the plunger stopper part are configured in such a manner that the plunger is required to be rotated by a predetermined angle in order to move further the plunger in a direction of a spray for the syringe barrel in the case in which the plunger is moved in a direction of the spray hole of the syringe barrel and the plunger side protruding part is abutted to the plunger stopper, whereby the spray of a plurality of times can be carried out.

By the above configuration, in the case in which the spray of the medicinal solution is carried out a plurality of times, the plunger side protruding part is abutted to the plunger stopper when one spray of the medicinal solution is completed. Since it is necessary to rotate the plunger by a predetermined angle in order to further move the plunger in a direction of a spray of the syringe barrel, the medicinal solution of an amount for a plurality of times can be prevented from being sprayed at once in the wrong, and the medicinal solution of an amount for once can be sprayed for every time with a certainty.

The prefilled type nasal drip appliance in accordance with the present invention is characterized in that a finger applying part in a flange shape that is protruded outside from the outer circumferential face of the syringe barrel is formed at a generally central position in a direction of an axis of the syringe barrel.

By the above configuration, in the case in which the syringe barrel is inserted into the nostril from the side of the spray hole, a finger that has been applied to the finger applying part is abutted to the nostril. Consequently, the syringe barrel is not inserted into the deeper part of the nostril more than necessary, and the prefilled type nasal drip appliance can be handled in safety to spray the medicinal solution into the nostril.

The prefilled type nasal drip appliance in accordance with the present invention is characterized in that the syringe barrel is formed by a molding in an integrated manner.

By forming the syringe barrel by a molding in an integrated manner as described above, a production speed becomes higher, a number of components that configure the syringe barrel can be reduced, and the syringe barrel can be produced with a high dimensional accuracy.

The prefilled type nasal drip appliance in accordance with the present invention is characterized in that the plunger that is attached to the piston is configured in a detachable manner to the piston.

As described above, in the case in which the plunger is configured in a detachable manner to the piston, the piston cannot be moved in a direction of an axis of the syringe barrel unless the plunger is attached to the piston until when the prefilled type nasal drip appliance is used. Consequently, the medicinal solution can be prevented from being sprayed in the wrong, and the prefilled type nasal drip appliance can be handled in safety with a certainty.

The prefilled type nasal drip appliance in accordance with the present invention is characterized in that a material of the syringe barrel is a cyclic olefin series resin.

Such a material has a high transparency and an excellent heat resistance property in particular and has no chemical interaction with a pharmacological product. Consequently, the material can be preferably used for a medical drug and a medical treatment.

The prefilled type nasal drip appliance in accordance with the present invention is characterized in that a tetrafluoroethylene film is laminated on the surface of the piston and the center stopper.

By the above configuration, the piston and the center stopper that are disposed in the syringe barrel can have both of a liquid-tight property and a sliding property in the syringe barrel.

By the present invention, for a prefilled type nasal drip appliance in particular among the nasal drip appliances, a prefilled type nasal drip appliance that enables a production cost thereof to be suppressed can be provided by reducing a number of components that configure the prefilled type nasal drip appliance and by simplifying the configuration of the prefilled type nasal drip appliance.

Moreover, it is possible to provide a prefilled type nasal drip appliance that can be handled by everyone in the same way, that can be easily handled, and that enables a medicinal solution to be sprayed into the nostril with a certainty.

BRIEF DESCRIPTION OF THE DRAWINGS

FIG. 18(a) is an exploded view, and FIG. 18(b) is a schematic cross-sectional view.

Figure 1:
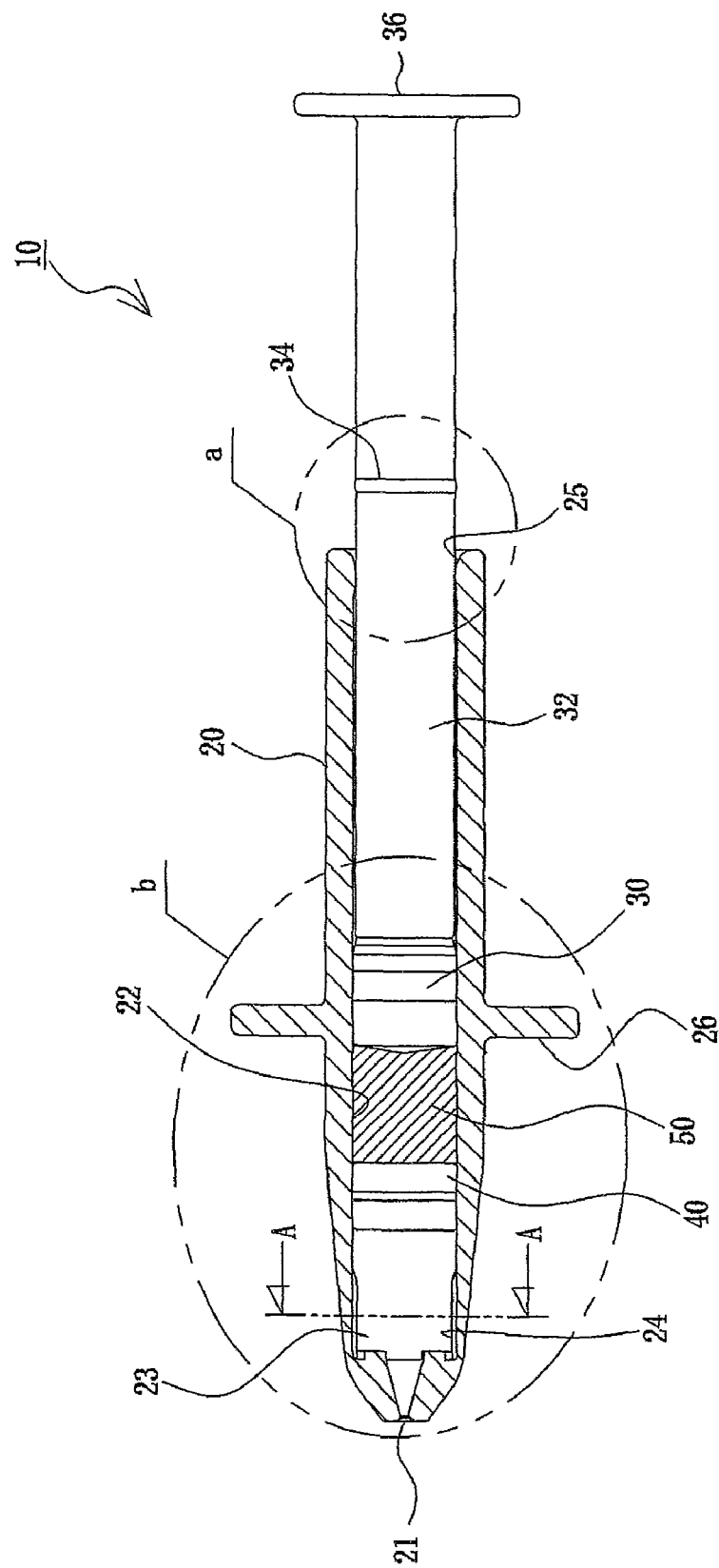
FIG. 1 is a schematic cross-sectional view showing a prefilled type nasal drip appliance in accordance with an embodiment of the present invention.

10: Prefilled type nasal drip appliance
20: Syringe barrel
21: Spray hole
22: Medical solution storage part
23: Center stopper locking part
24: Conduction part
25: Syringe barrel side protruding part
26: Finger applying part
27: Medical solution inflow groove
28: Flow path
29: Slope part
30: Piston
32: Plunger
34: Plunger side protruding part
34a: Plunger side first protruding part
34b: Plunger side second protruding part
36: Plunger rear end part
38: Groove
40: Center stopper
42: Groove
44: Plunger stopper
46 Cut part
47: Syringe barrel side identification mark
48: Plunger stopper part
49: Plunger side identification mark
50: Medical solution
R1: Outside dimension of the plunger
R2: Inner diameter dimension of the syringe barrel side protruding part
R3: Most outer diameter of the piston
R4: Most outer diameter dimension of the center stopper
L1: Length of the conduction part
L2: Length in a thickness direction of the center stopper
L3: Width in a plunger outer circumferential direction of the plunger side protruding part
L4: Width in a syringe barrel inner circumferential direction of the cut part
100: Nasal drip appliance
102: Syringe barrel
104: Plunger
106: Medical solution
108: Spray hole
200: Nasal drip appliance
202: Syringe barrel
204: Plunger
206: Medical solution
208: Spray hole
210: Introduction hole
212: Skirt valve
214: Adapter
216: Stopper
300: Nasal drip appliance
302: Syringe barrel
306: Medical solution
314: Adapter
318: Spray nozzle
320: Spray nozzle
400: Prefilled type nasal drip appliance
402: Syringe barrel
404: Plunger
406: Medical solution
500: Prefilled type nasal drip appliance
502: Syringe barrel
504: Plunger
504a: Gasket part
504b: Shaft part
506: Medical solution
512: Valve
514: Adapter An embodiment (example) of the present invention will be described below in detail with reference to the drawings.

EMBODIMENT 1

Figure 2:
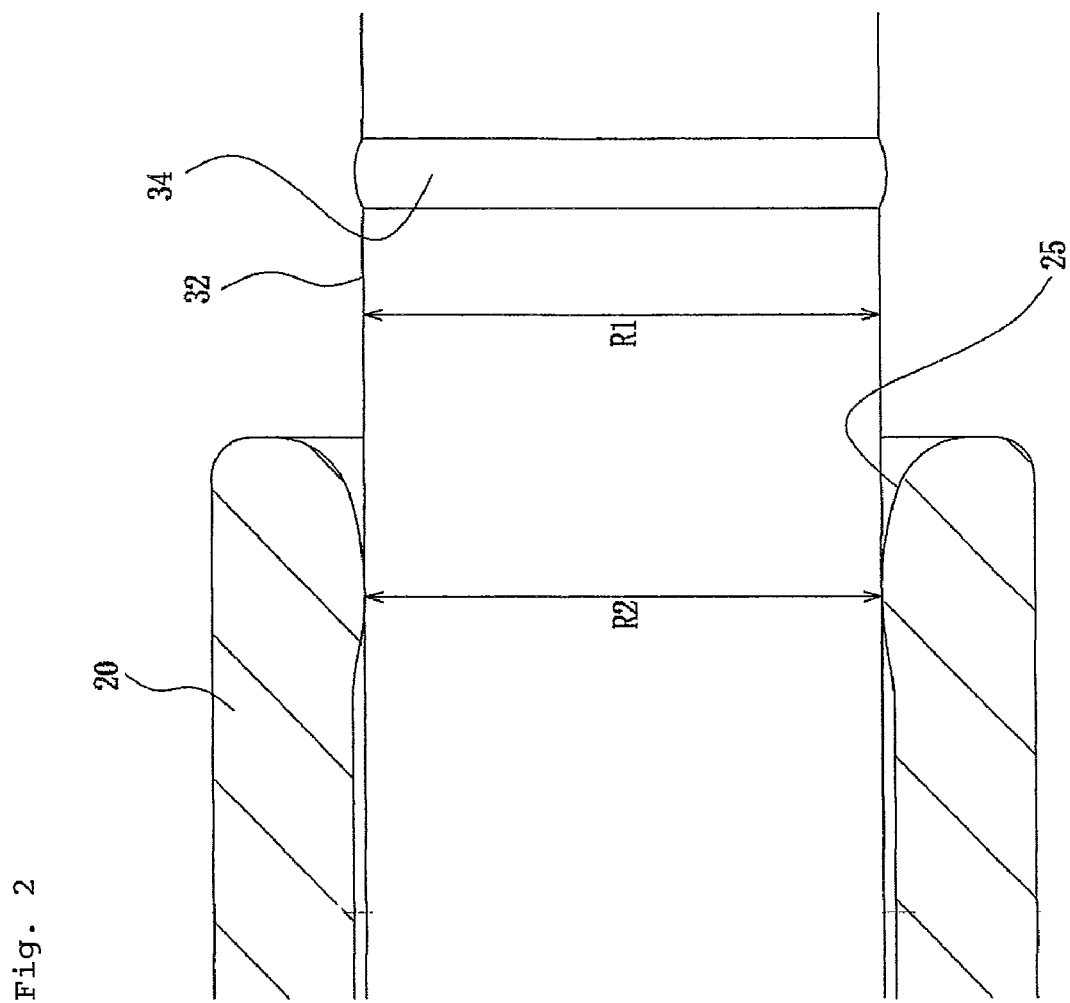
FIG. 2 is a partially enlarged view of the part a of the prefilled type nasal drip appliance shown in FIG. 1.
Figure 3:
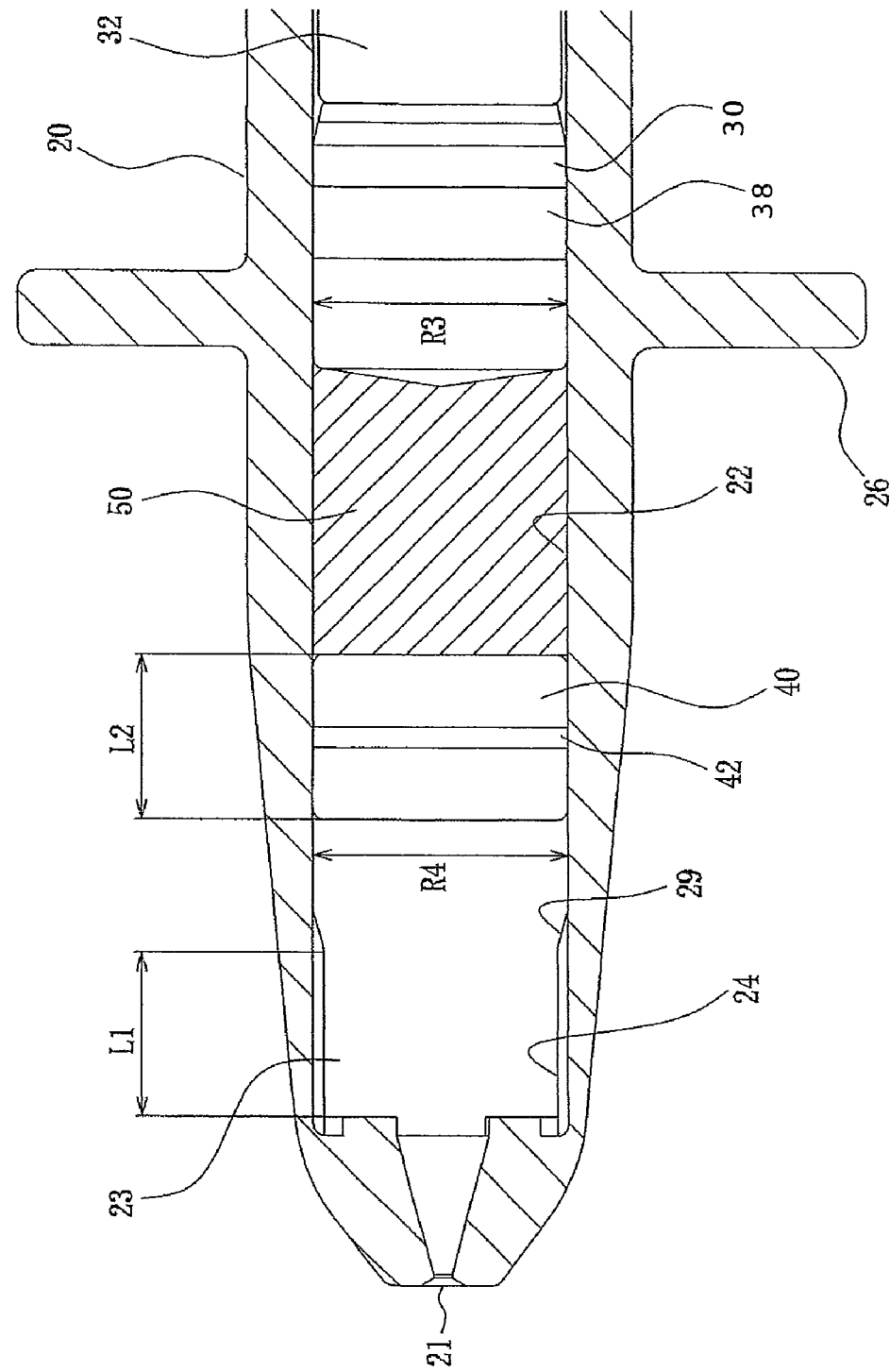
FIG. 3 is a partially enlarged view of the part b of the prefilled type nasal drip appliance shown in FIG. 1.
Figure 4:
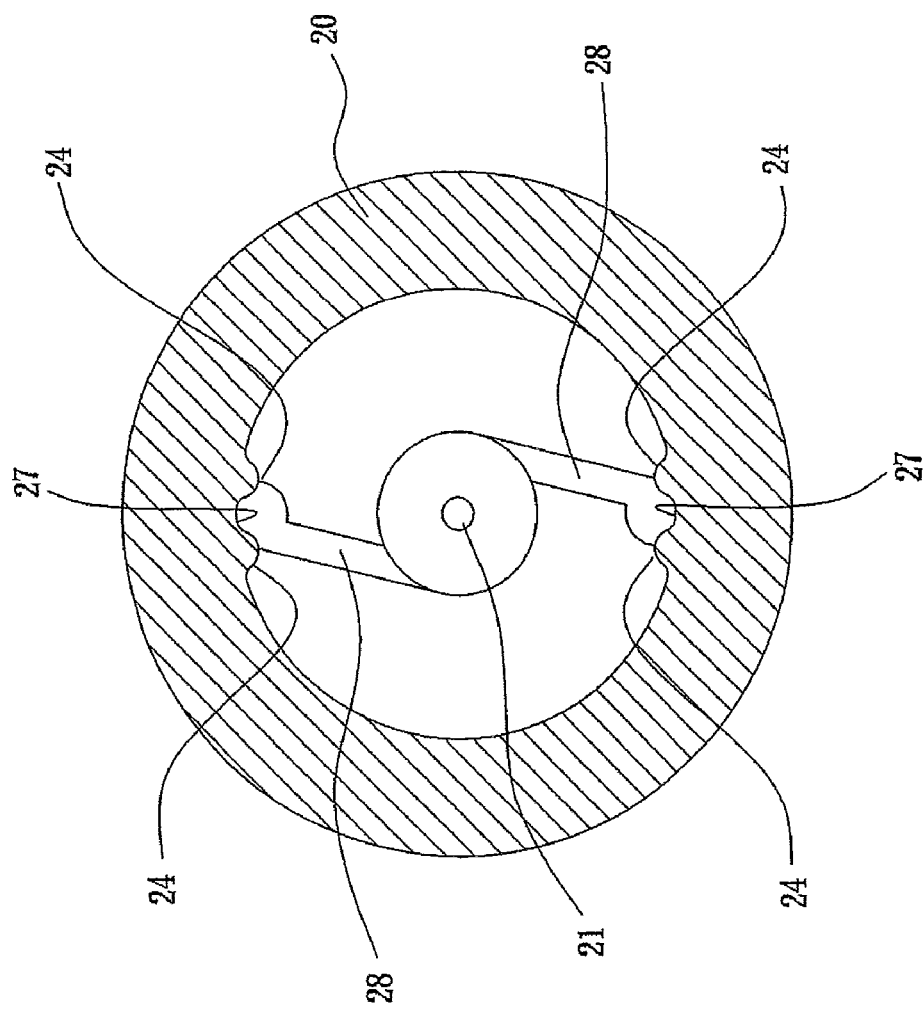
FIG. 4 is a cross-sectional view taken along the line A-A of the prefilled type nasal drip appliance shown FIG. 1.

FIG. 1 is a schematic cross-sectional view showing a prefilled type nasal drip appliance in accordance with an embodiment of the present invention. FIG. 2 is a partially enlarged view of the part a of the prefilled type nasal drip appliance shown in FIG. 1. FIG. 3 is a partially enlarged view of the part b of the prefilled type nasal drip appliance shown in FIG. 1. FIG. 4 is a cross-sectional view taken along the line A-A of the prefilled type nasal drip appliance shown FIG. 1.

A prefilled type nasal drip appliance in accordance with the present invention enables a medicinal solution in a syringe barrel to be sprayed into the nostril with a certainty by storing and retaining a medicinal solution in the syringe barrel in advance and by moving a plunger in a direction of an axis of the syringe barrel.

As shown in FIG. 1, a prefilled type nasal drip appliance 10 in accordance with the present invention is configured to be provided with a syringe barrel 20 that includes a spray hole 21 of a medicinal solution 50 on one side and a medical solution storage part 22 that stores and retains the medicinal solution 50 in advance on the other side, a piston 30 that is inserted into a syringe barrel 20 in a slidable manner to the inner circumferential face of the syringe barrel 20 and that has an elasticity, a plunger 32 that is attached to the rear end of the piston 30 and that enables the piston 30 to be moved in a direction of an axis of the syringe barrel 20, and an elastic center stopper 40 that is inserted into the syringe barrel 20 in such a manner that the center stopper 40 is located between the spray hole 21 of the syringe barrel 20 and the piston 30 and that can slide on the inner circumferential face of the syringe barrel 20. The medicinal solution 50 is stored and retained between the center stopper 40 and the piston 30 in a liquid-tight state in advance.

In the present embodiment of the present invention, the plunger 32 is screwed into the piston 30. However, the present invention is not restricted to this configuration, and the plunger can also be fitted to the piston for instance. The point is that any configuration can also be adopted providing the piston 30 and the plunger 32 can be detached from each other as needed and the members of the piston 30 and the plunger 32 are prevented from being detached when being used.

For the prefilled type nasal drip appliance 10 that has been configured as described above, the syringe barrel 20 is provided with a center stopper locking part 23 between the spray hole 21 and the center stopper 40, and a passage way that introduces the medicinal solution 50 is formed in the center stopper locking part 23. The form of the passage way can be a plurality of conduction parts 24 that are protruded inside from the inner circumferential face of the syringe barrel 20 like the present embodiment, and can be other bypass passage way. The point is that an introducing means of the medicinal solution 50 is formed in the configuration.

Moreover, a syringe barrel side protruding part 25 that is protruded inside from the inner circumferential face of the syringe barrel 20 is formed at the end on the other side from the spray hole 21 of the syringe barrel 20. On the other hand, a plunger side protruding part 34 that is protruded outside from the outer circumferential face of the plunger 32 is formed at a generally central part in a direction of an axis of the plunger 32.

As shown in FIG. 2, in the case in which the plunger 32 is moved in a direction of an axis of the syringe barrel 20, the syringe barrel side protruding part 25 and the plunger side protruding part 34 are configured to be engaged with each other. In the case in which the plunger 32 is moved in a direction of the spray hole 21 of the syringe barrel 20 and the plunger side protruding part 34 gets over the syringe barrel side protruding part 25, the engagement with each other is released according to a procedure for using a prefilled type nasal drip appliance as described later. Consequently, the medicinal solution 50 can be sprayed from the spray hole 21 with a certainty by a force for pressing the plunger 32 at this time.

In the case in which the plunger 32 is moved in a direction of the spray hole 21 of the syringe barrel 20 and the plunger side protruding part 34 gets over the syringe barrel side protruding part 25 for releasing the engagement with each other, a pressure of a predetermined level or more is specified to be required for the release.

In the case in which an outside dimension R1 of the plunger 32 is almost equivalent to an inner diameter dimension R2 of the syringe barrel side protruding part 25, and in the case in which the plunger 32 is moved in a direction of an axis of the syringe barrel 20, an external surface of the syringe barrel side protruding part 25 and an external surface of the plunger 32 slightly come into contact with each other to play a role as a guide, whereby the plunger 32 can be moved straight in a direction of an axis of the syringe barrel 20 preferably.

Moreover, as shown in FIG. 3 or 4, a plurality of the conduction parts 24 of the syringe barrel 20 are formed at a predetermined interval along the axis of the syringe barrel 20 to the center stopper locking part 23. As shown in FIG. 4, a cross sectional shape of the conduction part 24 is in a generally semicircular shape, and a medical solution inflow groove 27 is formed between the two conduction parts 24.

In the present embodiment, the conduction part 24 is formed at four locations, and therefore two medical solution inflow grooves 27 are formed. However, the number and a cross sectional shape of the conduction parts 24 and the medical solution inflow grooves 27 are not restricted to the configuration of the present embodiment. A formed location and a shape can be selected as needed, and a conduction part 24 in a protruding shape, in a groove shape, or of an expanded diameter type can also be illustrated for instance. However, it is preferable that a cross sectional shape of the conduction part 24 is a curved cross sectional shape since the center stopper 40 slides to and gets over the conduction part 24 as described later.

Moreover, in the case in which the prefilled type nasal drip appliance 10 is used, the center stopper 40 gets over the conduction part 24 and the medical solution inflow groove 27 for the medical solution 50 is formed. Consequently, for a forming range of the conduction part 24, it is preferable that a length L1 of the conduction part 24 is equivalent to a length L2 in a thickness direction of the center stopper 40, or a length L1 of the conduction part 24 is equivalent to or larger than a width of a contact part of the center stopper that comes into contact with the syringe barrel.

A slope part 29 is formed at the end part of the conduction part 24 on the side of the medical solution storage part 22. By this configuration, in the case in which the center stopper 40 is moved, the center stopper 40 can smoothly get over the conduction part 24.

It is preferable that a most outer diameter dimension R3 of the piston 30 and a most outer diameter dimension R4 of the center stopper 40 are specified in such a manner that the medical solution 50 in the syringe barrel 20 can be held in a liquid-tight state as well as the piston 30 and the center stopper 40 can be moved in the syringe barrel 20, that is, in such a manner that the appliance is provided with both of a liquid-tight property and a sliding property.

Moreover, a finger applying part 26 in a flange shape is formed on the outer circumferential face of the syringe barrel 20 and at a generally central position in a direction of an axis of the syringe barrel 20. The finger applying part 26 is used for applying a force by hanging fingers in the case in which the plunger 32 is moved. In addition, in the case in which the spray hole 21 side of the prefilled type nasal drip appliance 10 is inserted into the nostril, the finger applying part 26 plays a role as a stopper in order to prevent the prefilled type nasal drip appliance 10 from being inserted into the deepest part of the nostril and from injuring the nostril floor.

For the prefilled type nasal drip appliance 10 that has been configured as described above, the plunger 32 is moved in a direction of an axis of the syringe barrel 20 on the side of the spray hole 21, and the plunger side protruding part 34 gets over the syringe barrel side protruding part 25 for releasing the engagement with each other. Consequently, in the case in which a plunger rear end part 36 of the plunger 32 is pressed toward the side of the spray hole 21 of the syringe barrel 20 in the state in which fingers are hung on the finger applying part 26 of the syringe barrel 20, the plunger side protruding part 34 gets over the syringe barrel side protruding part 25 to release the engagement with each other. In addition, the medicinal solution 50 can move the center stopper 40 in a direction of the spray hole 21 by a force for pressing the plunger 32.

Subsequently, the center stopper 40 gets over the conduction part 24 that has been formed to the center stopper locking part 23, and the medical solution inflow groove 27 is formed between the conduction part 24 and the center stopper 40, whereby the medical solution storage part 22 and the spray hole 21 are interconnected with each other.

In the present embodiment, as shown in FIG. 4, two medical solution inflow grooves 27 are formed, and a flow path 28 that is interconnected with the spray hole 21 is formed for the medical solution inflow groove 27. Consequently, in the case in which the center stopper 40 gets over the conduction part 24, the medicinal solution 50 is moved through the medical solution inflow groove 27 and the flow path 28 to the spray hole 21. By the above configuration, the medicinal solution 50 is then sprayed from the spray hole 21.

In other words, in the case in which a plunger rear end part 36 of the plunger 32 is pressed toward the side of the spray hole 21 of the syringe barrel 20 and the plunger side protruding part 34 gets over the syringe barrel side protruding part 25 to release the engagement with each other, a pressure of a predetermined level or more is required. At this time, the center stopper 40 is made to get over the conduction part 24 by a pressing force that is applied to the plunger 32, and the medicinal solution 50 is then sprayed from the spray hole 21. Consequently, a failure in which the medicinal solution 50 is not sprayed into the nostril due to a lack of a spray pressure can be prevented, and everyone can spray the medicinal solution 50 into the nostril at any time with a certainty.

A hole diameter of the spray hole 21 that is formed at one end part of the syringe barrel 20 can be determined properly depending on a spray amount of the medicinal solution 50 and a pressing force that is applied to the plunger 32. However, it is preferable that the hole diameter of the spray hole 21 is specified to be a degree in which a surface tension is applied in such a manner that the medicinal solution 50 does not leak in the case in which the spray hole 21 is faced downward.

Moreover, it is necessary that the piston 30 that is used for the prefilled type nasal drip appliance 10 that has been configured as described above has both of a liquid-tight property and a sliding property in the syringe barrel 20. As a material of the piston 30, a rubber material that has been used conventionally and that are described in the following is used preferably.

As a rubber material, there can be mentioned for instance a butyl series rubber such as a butyl rubber, a chlorinated butyl rubber, a brominated butyl rubber, and a divinylbenzene copolymerization butyl rubber; a conjugated diene series rubber such as a polyisoprene rubber, (high to low cis 1, 4 bonding), a polybutadiene rubber (high to low cis 1, 4 bonding), and a styrene-butadiene copolymerization rubber; and a thermoplastic elastomer such as an ethylene-propylene-diene terpolymerization rubber (EPDM), a styrene-ethylene-butadiene copolymer (SEBS), a block copolymer of styrene-butadiene-styrene (SBS), a styrene-isoprene block copolymer (SIS), and a styrene-isobutylene block copolymer (SIBS).

A thermoplastic elastomer is a material of a kind different from that of a rubber material in a precise sense. However, the thermoplastic elastomer is used similarly to a rubber material in the fields of the present invention. Consequently, a rubber material in accordance with the present invention includes a thermoplastic elastomer.

The piston 30 is produced by using a crosslinking rubber composition (compound) that is obtained by kneading the above rubber material and a compounding agent such as a crosslinking agent, a filler and/or a reinforcing agent, a coloring agent, and an age resister as needed and by a publicly known molding method such as a compression molding and an injection molding for a piston.

A compounding agent to be used is not restricted in particular, and can be a compounding agent that has been used in producing a rubber stopper or a piston for a pharmacological product or medical treatment tools.

Moreover, it is preferable that the surface of the piston 30 is laminated by a laminate film. The entire of the piston 30 can be laminated, and only a part that comes into contact with the medicinal solution 50 can be laminated partially. It is preferable that the lamination is selected properly depending on the environment of usage.

As such a laminate film, a publicly known laminate film can be used, and the laminate film is not restricted in particular. As a material of a laminate film, there can be mentioned for instance a fluorine series resin, polypropylene, polyethylene, ultrahigh molecular weight polyethylene, and tetrafluoroethylene.

It is necessary that the center stopper 40 that is used for the prefilled type nasal drip appliance 10 has both of a liquid-tight property and a sliding property similarly to the piston 30 as described above. It is preferable that the surface of the center stopper 40 is laminated by a laminate film. As the material of the center stopper 40 and the laminate film, those similar to those of the piston 30 can be used preferably.

Moreover, for the piston 30 and the center stopper 40 that are configured as described above, as shown in FIG. 3, the grooves 38 and 42 are preferably formed at a region that comes into contact with the inner circumferential face of the syringe barrel 20 in order to reduce an area of contact with the inner circumferential face of the syringe barrel 20. The grooves 38 and 42 are formed for maintaining a liquid-tight property of the medicinal solution 50 in the syringe barrel 20 as well as for ensuring a sliding property of the piston 30 and the center stopper 40 similarly to a preferable selection of a material. Consequently, it is preferable that the forming conditions of the grooves 38 and 42 are adjusted in such a manner that both of the liquid-tight property and the sliding property can be ensured.

In the present embodiment, the grooves 38 and 42 are formed in parallel separately toward the direction of an axis of the syringe barrel 20. However, the shape of the grooves 38 and 42 is not restricted to the above configuration, and any shape can also be adopted providing an area of contact with the inner circumferential face of the syringe barrel 20 can be reduced and both of the liquid-tight property and the sliding property can be ensured.

As a material of the syringe barrel 20, a plastic that is suitable for an application is preferably used in general, and there can be mentioned for instance a cyclic olefin series resin, a cyclic olefin ethylene copolymer, a polyethylene terephthalate series resin, a polystyrene resin, and a polyethylene terephthalate resin. In particular, it is preferable to use a cyclic olefin series resin and a cyclic olefin ethylene copolymer that have a high transparency and an excellent heat resistance property and that have no chemical interaction with a pharmacological product (for instance, those used for a hygiene container disclosed in Patent Publication No. 2914826).

A material of the plunger 32 is not restricted in the case in which the plunger 32 can be used for a medical drug and a medical treatment. However, as a material of the plunger 32, a material equivalent to that of the syringe barrel 20 can also be used. As described above, in the case in which the syringe barrel 20 and the plunger 32 of the prefilled type nasal drip appliance 10 are made of a resin, a number of components can be reduced and a production cost can be suppressed by carrying out a resin molding in an integrated manner for instance. Moreover, as a capacity of the prefilled type nasal drip appliance in accordance with the present invention, although a prefilled type nasal drip appliance having a large capacity can be produced, a capacity in the range of 0.1 to 1.0 ml is suitable for the prefilled type nasal drip appliance due to an application thereof.

The following describes a procedure for using the prefilled type nasal drip appliance 10 in accordance with the present invention.

Figure 5:
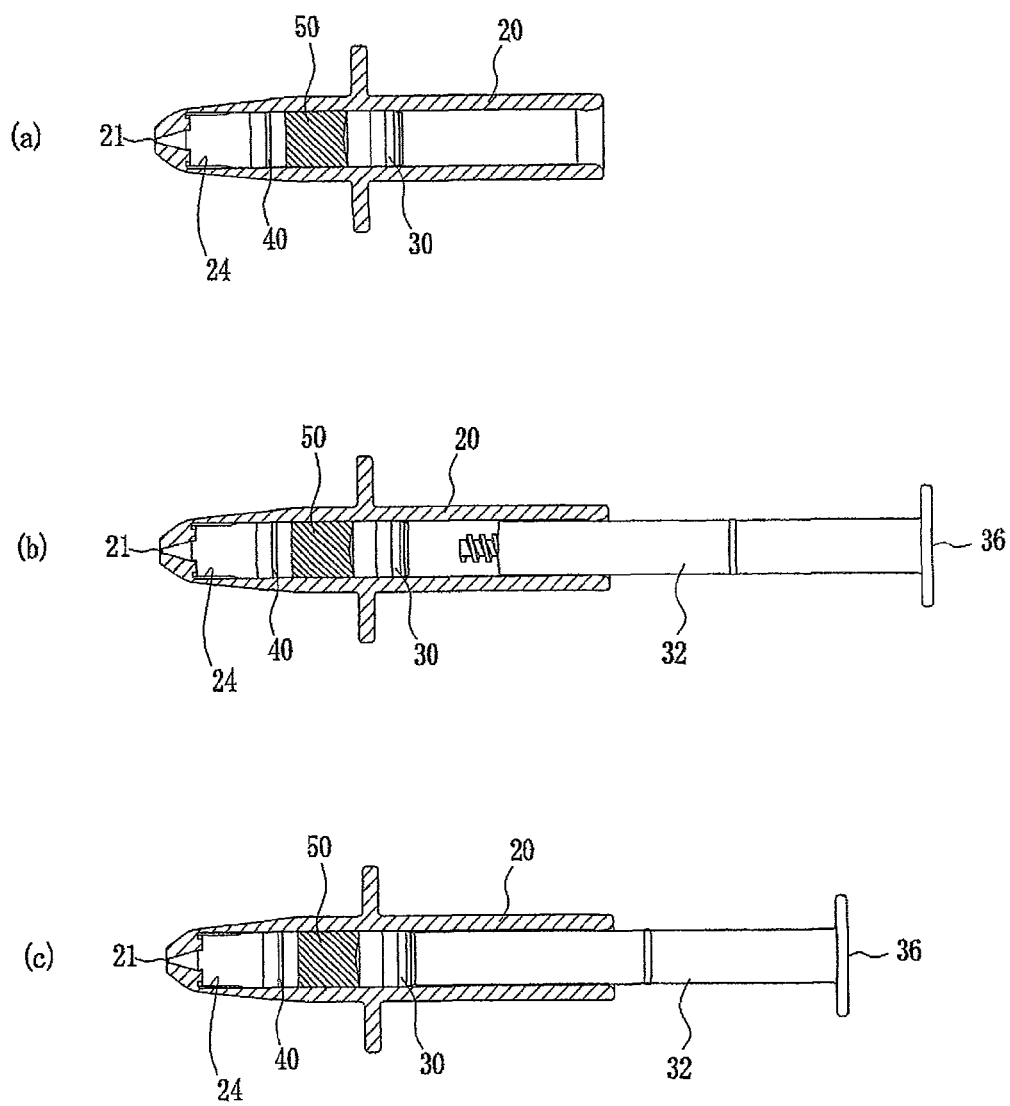
FIGS. 5(a) to 5(c) are the explanatory diagrams illustrating a procedure for using a prefilled type nasal drip appliance in accordance with the present invention.

At first, as shown in FIG. 5(a), the center stopper 40 is inserted into the syringe barrel 20 up to the front side of the conduction part 24, and the medicinal solution 50 of a predetermined amount is then filled in the syringe barrel 20. The piston 30 is then inserted into the syringe barrel 20 in such a manner that the medicinal solution 50 is sealed between the center stopper 40 and the piston 30 in a liquid-tight state. In the present embodiment, before the prefilled type nasal drip appliance 10 is used, a prefilled type nasal drip appliance in the state shown in FIG. 5(a) is produced in advance. When the prefilled type nasal drip appliance 10 is used, the produced prefilled type nasal drip appliance is then used according to the processes described later.

In the second place, as shown in FIG. 5(b), the plunger 32 is inserted into the rear end of the piston 30, and the plunger 32 is screwed into the piston 30 in such a manner that the piston 30 and the plunger 32 are integrated with each other as shown in FIG. 5(c).

In the case in which the prefilled type nasal drip appliance 10 is in the state in which the plunger 32 is detached from the piston 30 before a usage, the plunger rear end part 36 can be prevented from being pressed in the wrong, and the prefilled type nasal drip appliance 10 can be easily stored advantageously.

Moreover, as shown in FIG. 6(a), in the case in which the plunger 32 is pressed, the plunger side protruding part 34 is abutted to the syringe barrel side protruding part 25, and simultaneously the center stopper 40 is moved up to the position of the front end of the slope part 29 of the conduction part 24.

Moreover, as shown in FIG. 6(b), a pressure is applied to the plunger rear end part 36 in this state in such a manner that the plunger side protruding part 34 can get over the syringe barrel side protruding part 25, and the plunger side protruding part 34 then gets over the syringe barrel side protruding part 25. Subsequently, the medicinal solution 50 that has been pressed by the piston 30 presses the center stopper 40, and the center stopper 40 gets over the conduction part 24 entirely.

In the next place, as shown in FIG. 6(c), in the case in which the plunger rear end part 36 is pressed in addition, the medicinal solution 50 enters the flow path 28 through the medical solution inflow groove 27 that has been formed between the conduction part 24 and the center stopper 40, and the medicinal solution 50 is sprayed outside from the spray hole 21.

Figure 7:
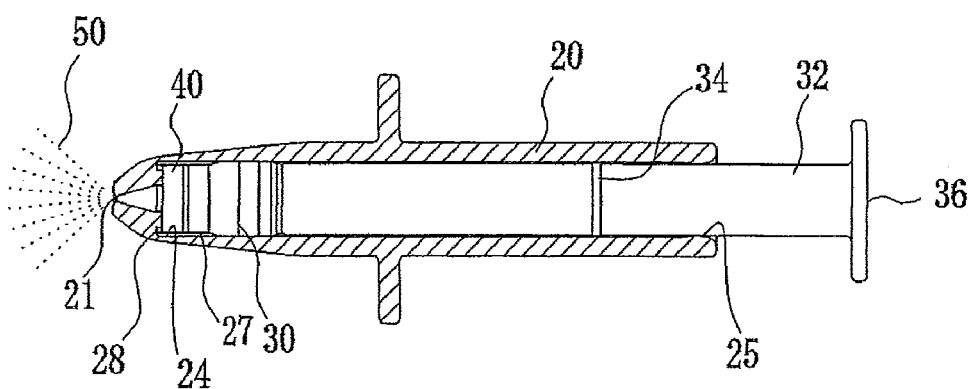
FIG. 7 is an explanatory diagram illustrating a procedure for using a prefilled type nasal drip appliance in accordance with the present invention.

Moreover, as shown in FIG. 7, in the case in which the plunger rear end part 36 is pressed and all of the medicinal solution 50 is sprayed outside from the spray hole 21 completely, a use of the prefilled type nasal drip appliance 10 is completed.

Figure 6:
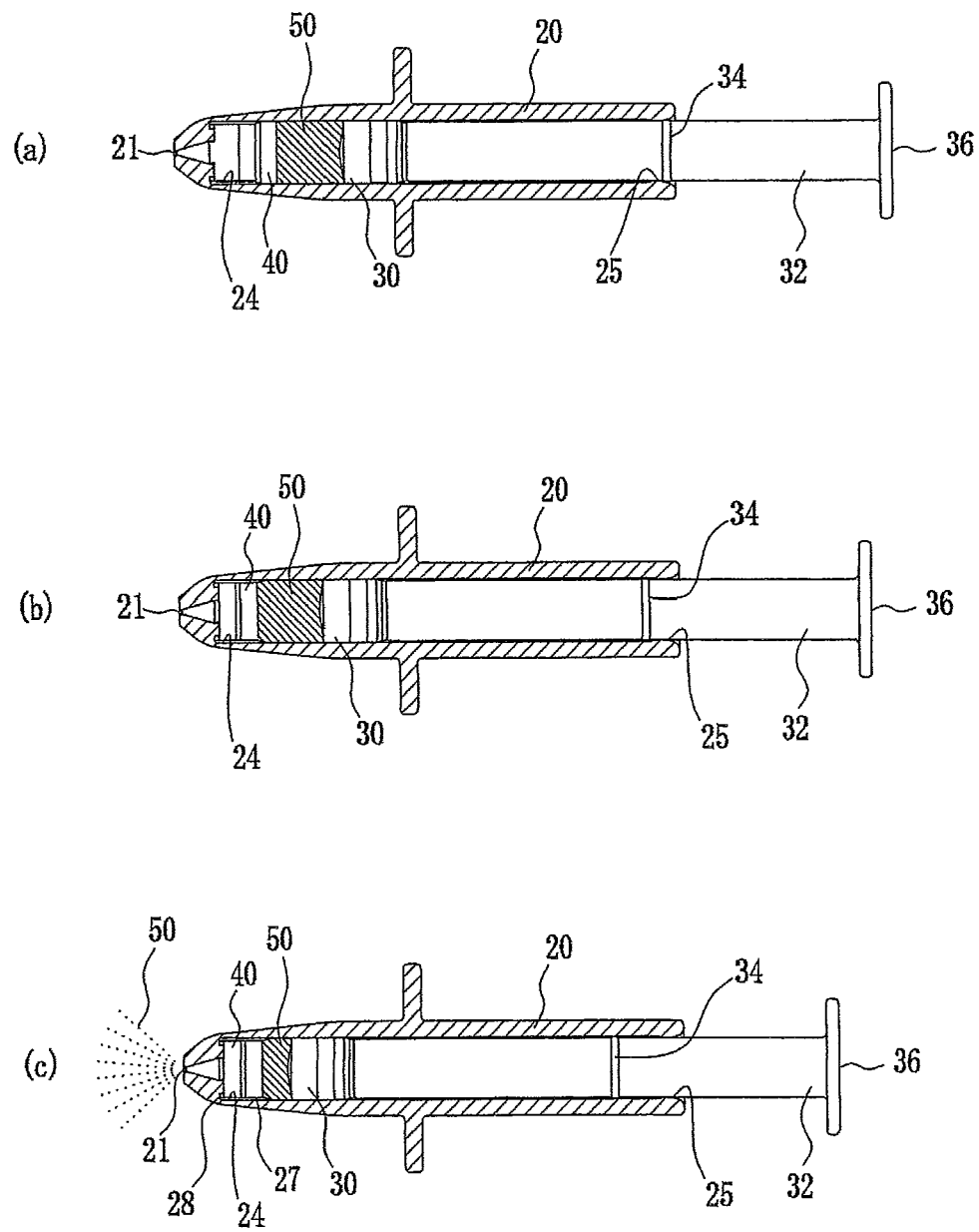
FIGS. 6(a) to 6(c) are the explanatory diagrams illustrating a procedure for using a prefilled type nasal drip appliance in accordance with the present invention.

For the procedure for using the prefilled type nasal drip appliance 10 as described above, the processes illustrated in FIGS. 5(c) to 7 are carried out in less than no time as a practical matter. The point is that, as shown in FIG. 6(a), by a pressing force of a predetermined level or more in the case in which the plunger side protruding part 34 gets over the syringe barrel side protruding part 25, each of the processes is carried out until the medicinal solution 50 is sprayed into the nostril.

By a pressing force of a predetermined level or more in the case in which the plunger side protruding part 34 gets over the syringe barrel side protruding part 25, the medicinal solution 50 can be sprayed from the spray hole 21 in the form of a liquid mist with a certainty.

EMBODIMENT 2

In the next place, another embodiment of the prefilled type nasal drip appliance 10 in accordance with the present invention will be described below in detail by using the explanatory diagrams shown in FIGS. 8(a) to 8(c).

Figure 8:
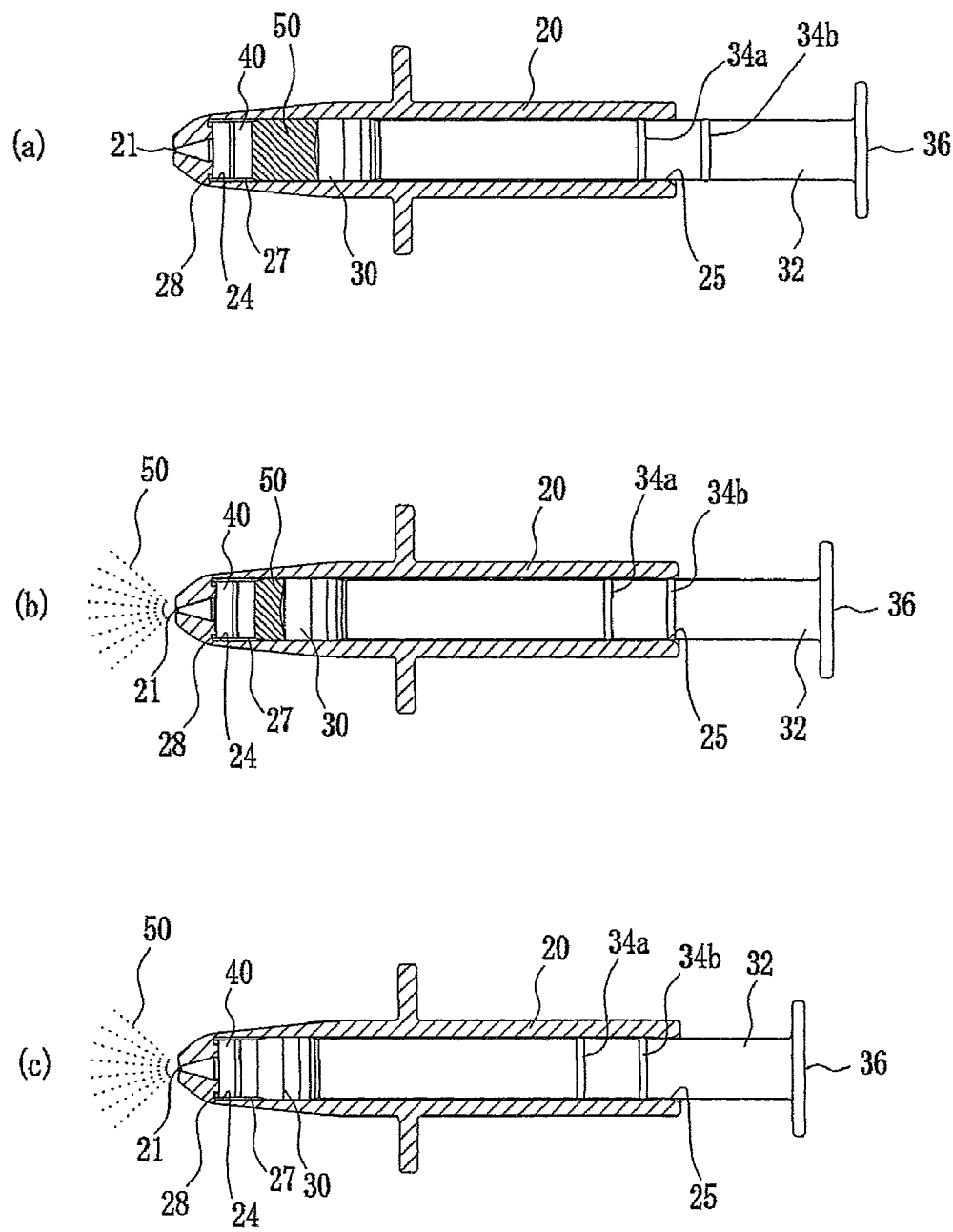
FIGS. 8(a) to 8(c) are the explanatory diagrams illustrating a procedure for using a prefilled type nasal drip appliance in accordance with another embodiment of the present invention.

The prefilled type nasal drip appliance 10 shown in FIGS. 8(a) to 8(c) has a configuration equivalent to that of the prefilled type nasal drip appliance 10 shown in FIGS. 1 to 7 in the elementary sense. Consequently, elements equivalent to those illustrated in FIGS. 1 to 7 are numerically numbered similarly and the detailed descriptions of the equivalent elements are omitted.

The prefilled type nasal drip appliance 10 in accordance with the present embodiment is different from the embodiment described above in the point that a plurality of the plunger side protruding parts 34 are formed on the plunger 32.

For the prefilled type nasal drip appliance 10 that has been configured as described above, as shown in FIG. 8(a), in the case in which a plunger side first protruding part 34a of the plunger 32 gets over the syringe barrel side protruding part 25, the piston 30 presses the medicinal solution 50 by a pressing force that is applied to the plunger 32 at that time. Moreover, the medicinal solution 50 makes the center stopper 40 to get over the conduction part 24, the medicinal solution 50 then flows into the flow path 28 through the medical solution inflow groove 27, and the medicinal solution 50 is sprayed outside from the spray hole 21.

Moreover, as shown in FIG. 8(b), in the case in which a plunger side second protruding part 34b of the plunger 32 is abutted to the syringe barrel side protruding part 25, the movement of the plunger 32 in a direction of an axis of the syringe barrel 20 is stopped, and a spray of the medicinal solution 50 is also stopped.

In the next place, as shown in FIG. 8(c), in the case in which the plunger rear end part 36 is pressed again and a pressure is applied to the plunger 32 in such a manner that the plunger side second protruding part 34b can get over the syringe barrel side protruding part 25, the remaining medicinal solution 50 is sprayed outside from the spray hole 21 similarly to the processes as described above.

As described above, in the case in which a plurality of the plunger side protruding parts 34 are formed on the plunger 32 and the syringe barrel 20 is filled with the medicinal solution 50 of an amount that enables the spray of a plurality of times corresponding to the number of the plunger side protruding parts 34, the spray can be carried out a plurality of times.

Consequently, even in the case in which a right nostril and a left nostril are sprayed separately for instance, or even in the case in which it is necessary to carry out a nasal drip a plurality of times at an outside location for instance, the spray of the medicinal solution 50 can be carried out a plurality of times by using one prefilled type nasal drip appliance 10 in accordance with the present embodiment. As a result, it is not necessary to possess a plurality of prefilled type nasal drip appliances 10, and the portability of the prefilled type nasal drip appliance 10 can be improved.

The present embodiment has described the example in which the plunger side protruding part 34 is formed at two locations to enable the spray of two times. However, the present invention is not restricted to the embodiment. The number of the plunger side protruding parts 34 can be increased corresponding to the number of times of sprays, and the number of the plunger side protruding parts 34 can be selected properly as needed.

EMBODIMENT 3

In the next place, another embodiment of the prefilled type nasal drip appliance 10 in accordance with the present invention will be described below in detail by using the explanatory diagrams shown in FIGS. 9 to 13(b).

Figure 9:
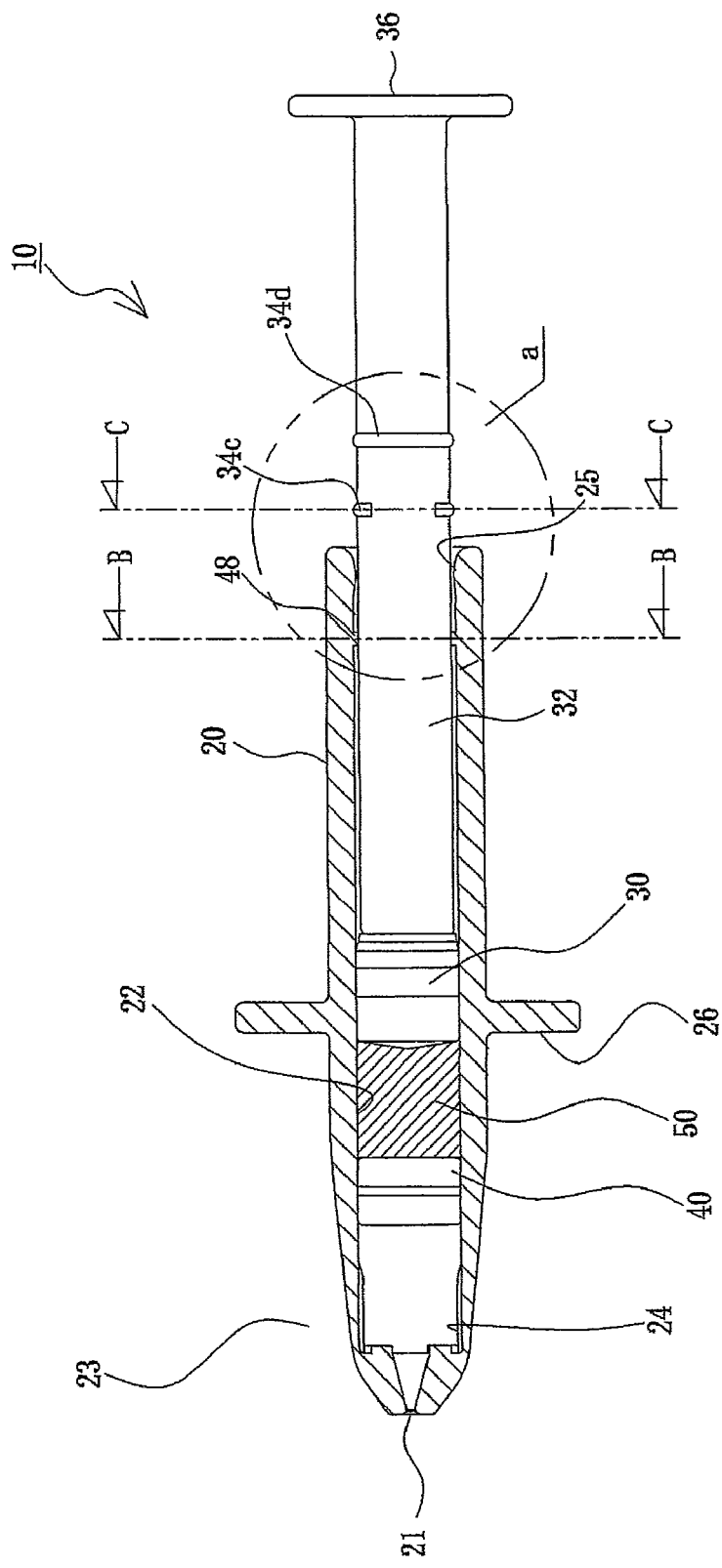
FIG. 9 is a schematic cross-sectional view showing a prefilled type nasal drip appliance 10 in accordance with another embodiment of the present invention.
Figure 10:
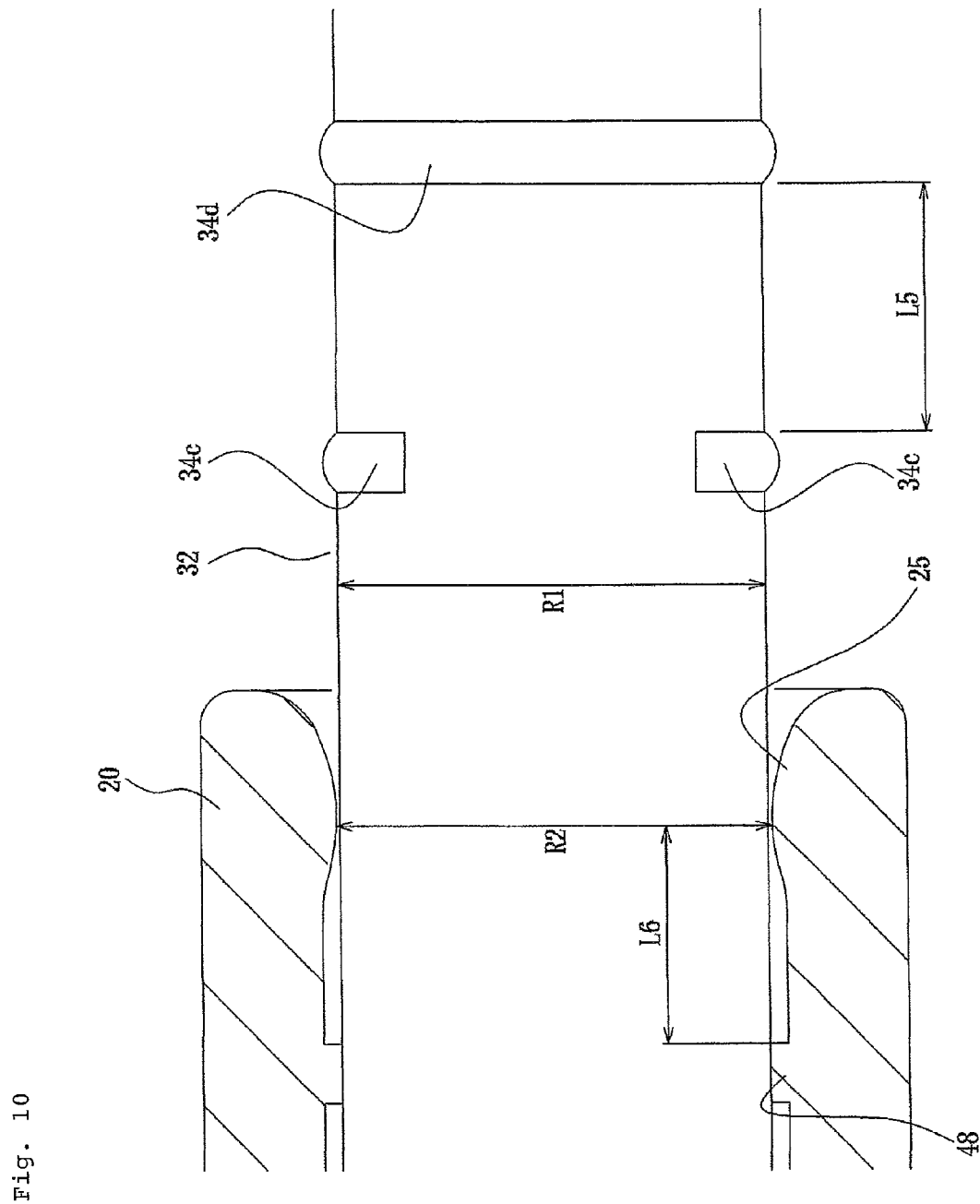
FIG. 10 is a partially enlarged view of the part a of the prefilled type nasal drip appliance shown in FIG. 9.
Figure 11:
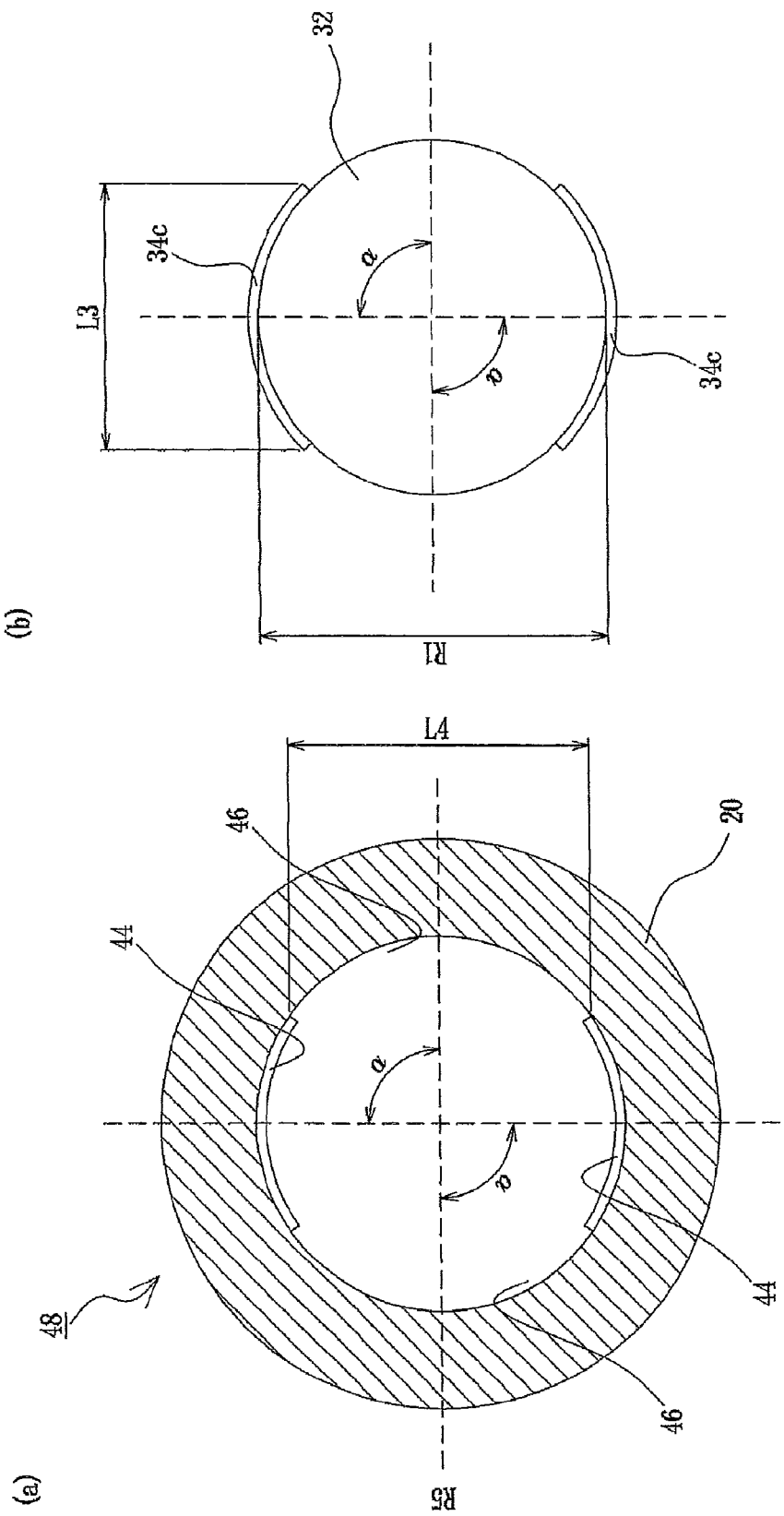
FIG. 11(a) is a cross-sectional view taken along the line B-B of the prefilled type nasal drip appliance shown FIG. 9.
FIG. 11(b) is a cross-sectional view taken along the line C-C of the prefilled type nasal drip appliance shown FIG. 9.
Figure 12:
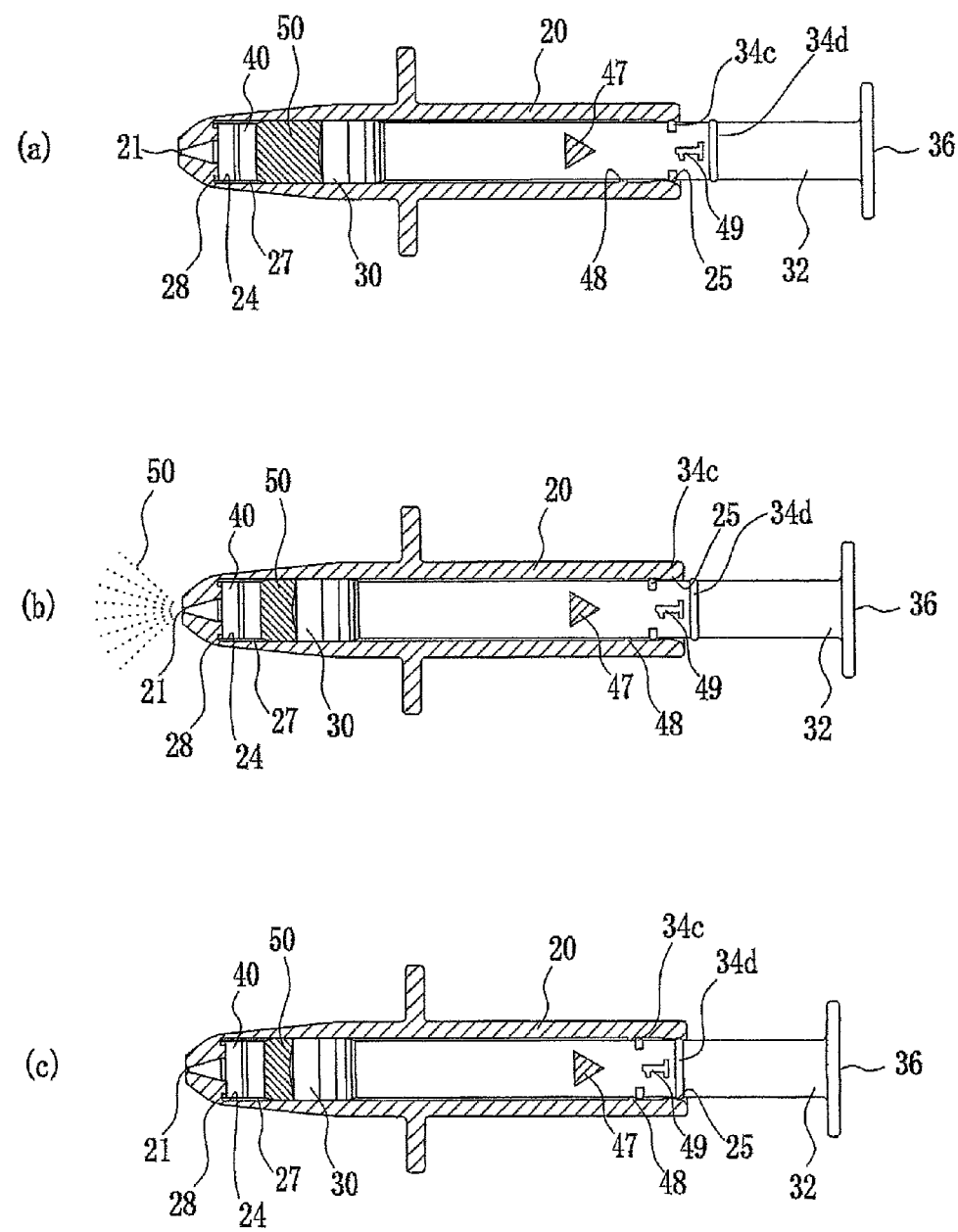
FIGS. 12(a) to 12(c) are the explanatory diagrams illustrating a procedure for using a prefilled type nasal drip appliance in accordance with another embodiment of the present invention.
Figure 13:
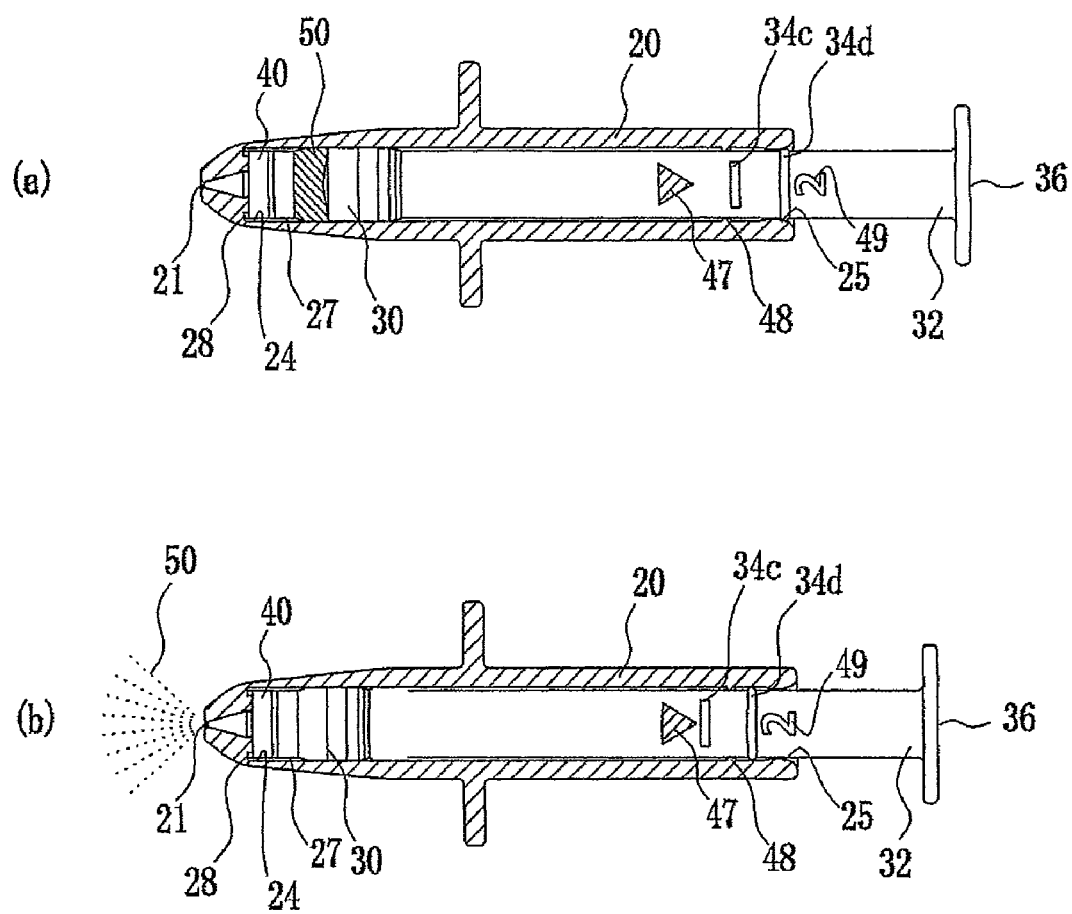
FIGS. 13(a) and 13(b) are the explanatory diagrams illustrating a procedure for using a prefilled type nasal drip appliance in accordance with another embodiment of the present invention.
Figure 14:
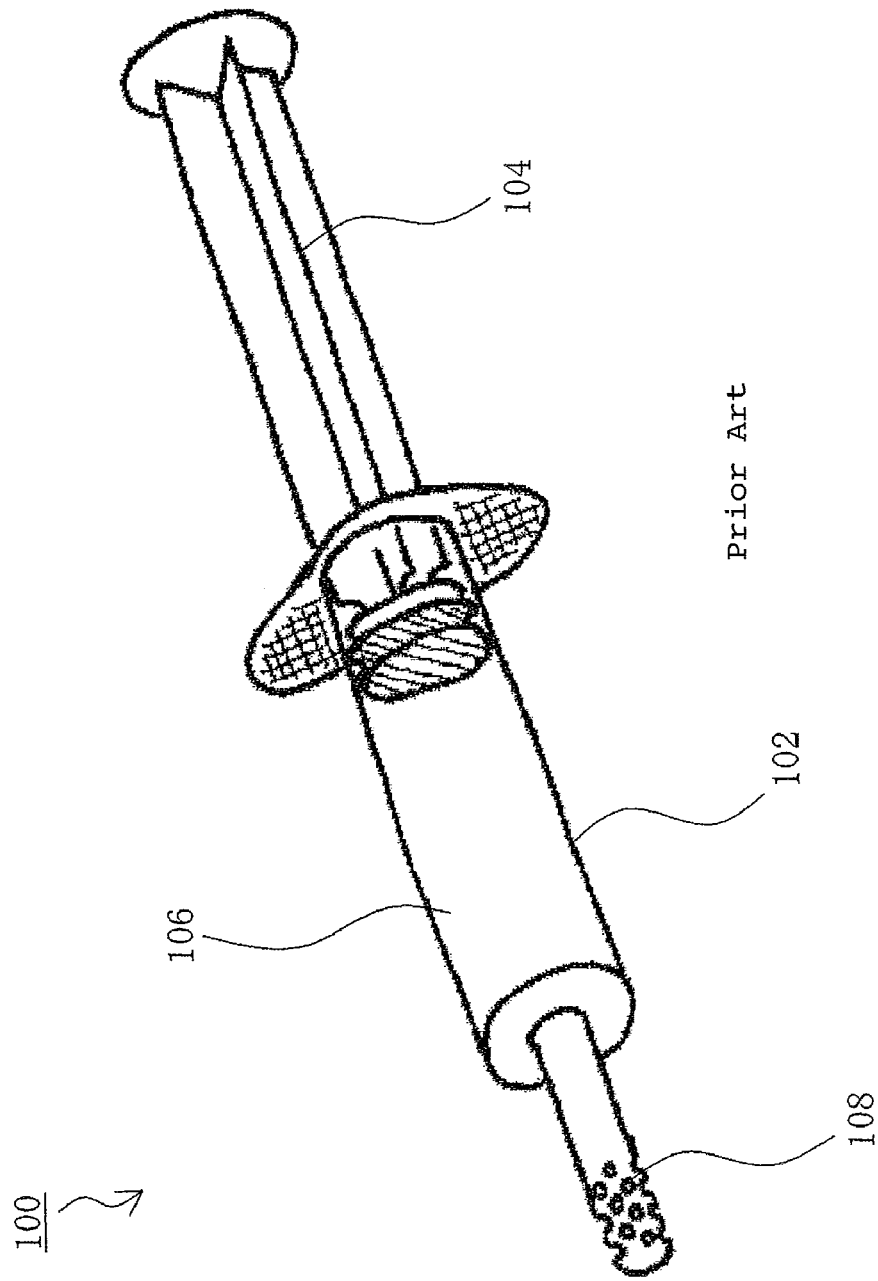
FIG. 14 is a perspective view showing a conventional nasal drip appliance.
Figure 15:
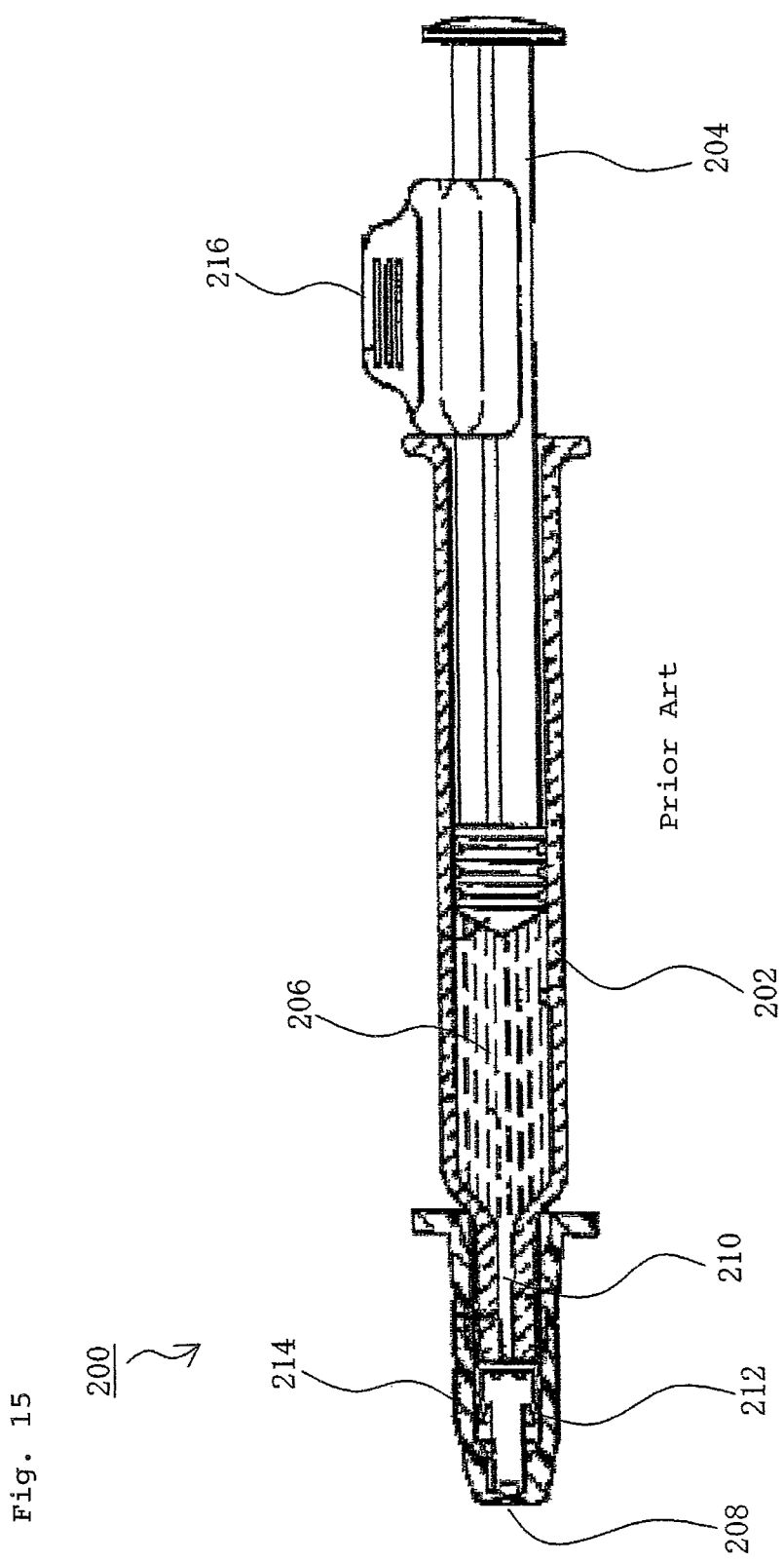
FIG. 15 is a schematic cross-sectional view showing a conventional nasal drip appliance.
Figure 16:
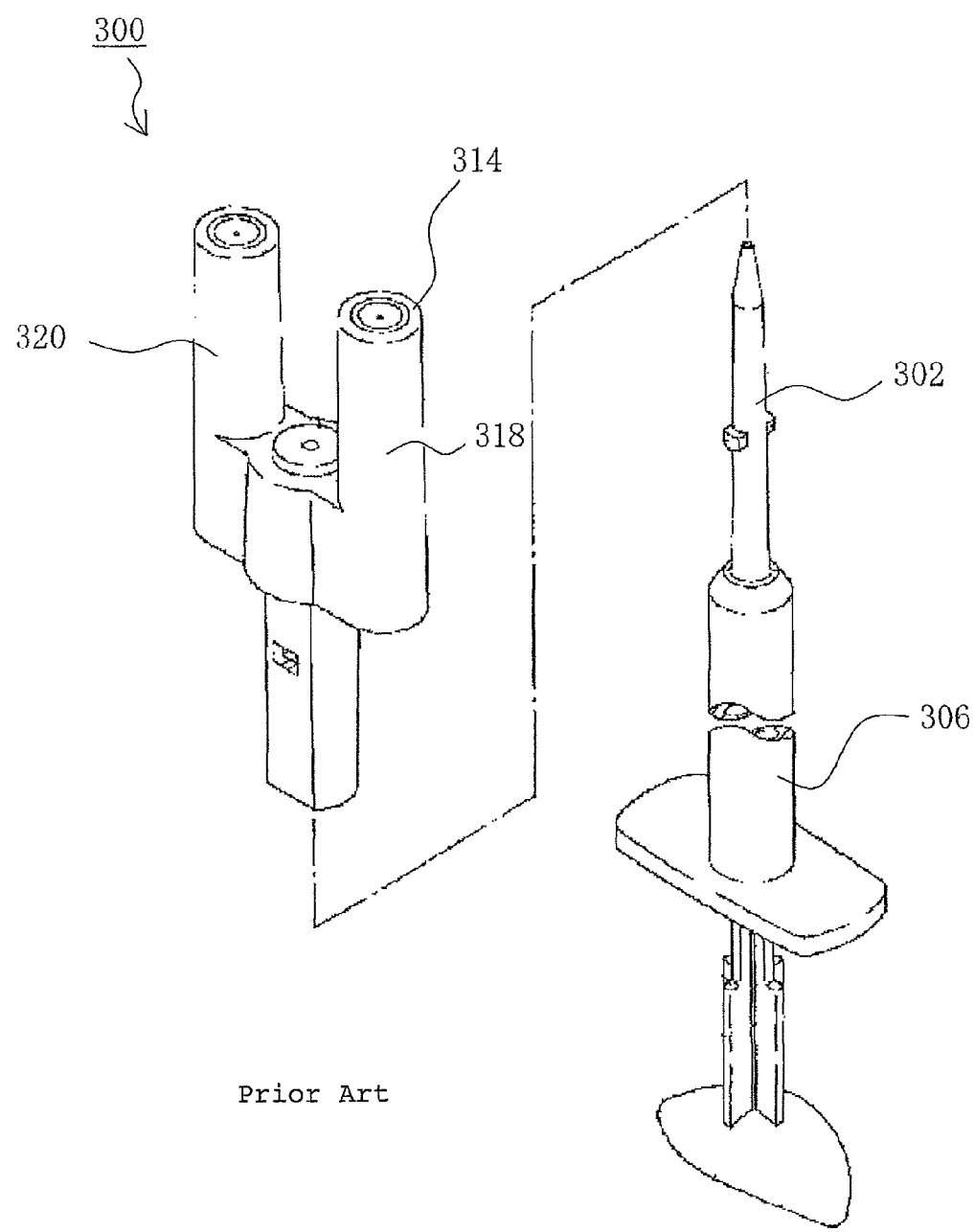
FIG. 16 is an exploded perspective view showing a conventional nasal drip appliance.
Figure 17:
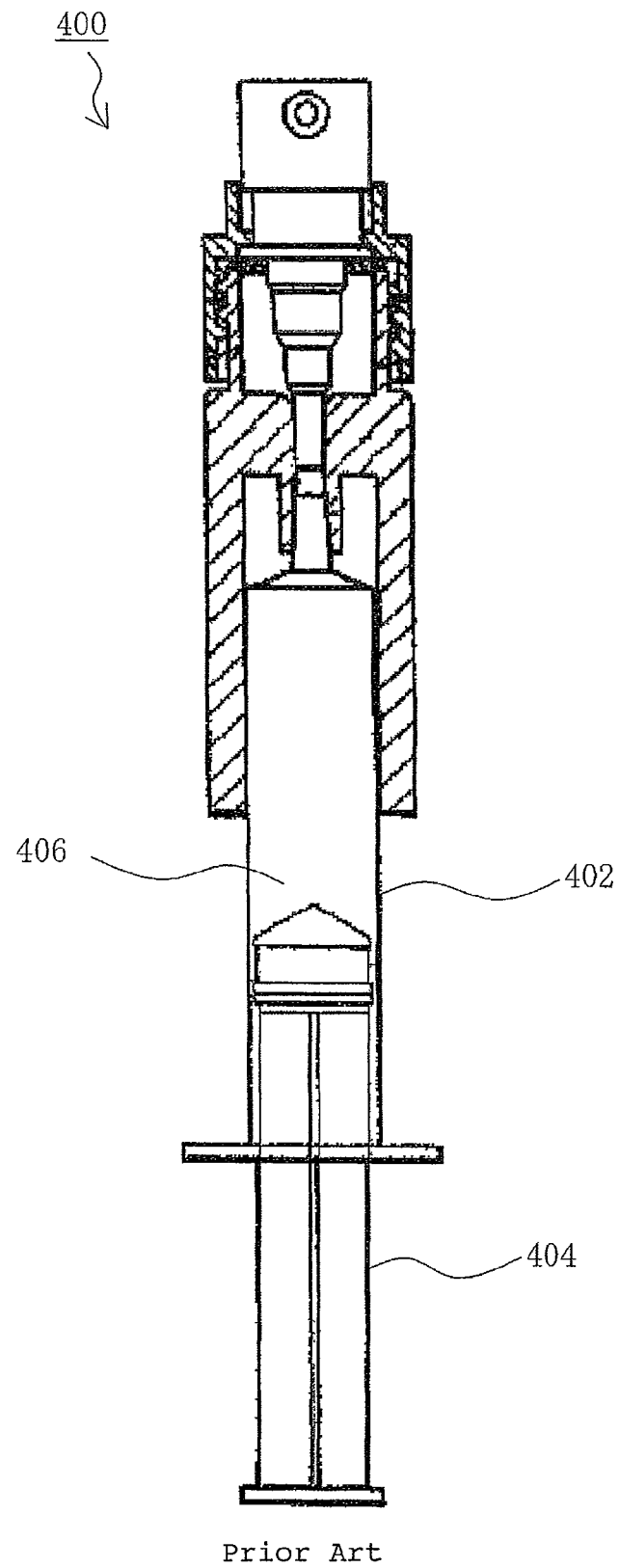
FIG. 17 is a schematic cross-sectional view showing a conventional prefilled type nasal drip appliance.
Figure 18:
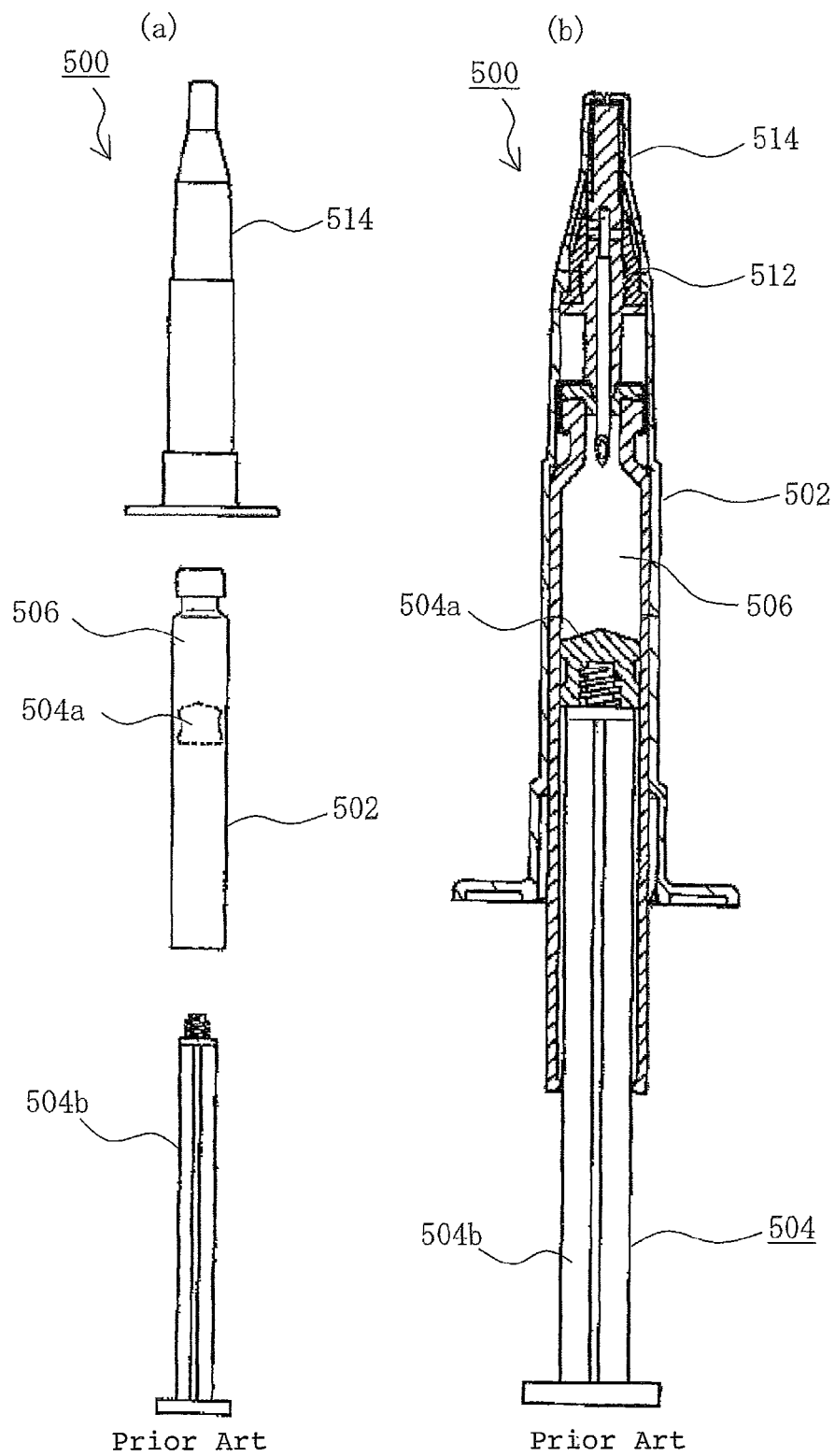
FIG. 18 is a view showing a conventional prefilled type nasal drip appliance.

FIG. 9 is a schematic cross-sectional view showing a prefilled type nasal drip appliance 10 in accordance with another embodiment of the present invention. FIG. 10 is a partially enlarged view of the part a of the prefilled type nasal drip appliance shown in FIG. 9. FIG. 11(a) is a cross-sectional view taken along the line B-B of the prefilled type nasal drip appliance shown FIG. 9, and FIG. 11(b) is a cross-sectional view taken along the line C-C of the prefilled type nasal drip appliance shown FIG. 9. FIGS. 12(a) to 12(c) are the explanatory diagrams illustrating a procedure for using a prefilled type nasal drip appliance in accordance with another embodiment of the present invention. FIGS. 13(a) and 13(b) are the explanatory diagrams illustrating a procedure for using a prefilled type nasal drip appliance in accordance with another embodiment of the present invention.

The prefilled type nasal drip appliance 10 shown in FIGS. 9 to 13(b) has a configuration equivalent to that of the prefilled type nasal drip appliance 10 shown in FIGS. 1 to 7 in the elementary sense. Consequently, elements equivalent to those illustrated in FIGS. 1 to 7 are numerically numbered similarly and the detailed descriptions of the equivalent elements are omitted.

The prefilled type nasal drip appliance 10 in accordance with the present embodiment is different from the embodiment described above in the point that a plurality of the plunger side protruding parts 34 are formed on the plunger 32 and a plunger stopper part 48 is formed on the syringe barrel 20, whereby the spray of a plurality of times can be carried out, that is, the plunger side protruding parts 34 and the plunger stopper part 48 are configured in such a manner that the plunger 32 is required to be rotated by a predetermined angle in order to move the plunger 32 in a direction of a spray for the syringe barrel 20.

As shown in FIGS. 9 and 10, for the prefilled type nasal drip appliance 10 in accordance with the present embodiment, two plunger side protruding parts composed of a plunger side first protruding part 34c and a plunger side second protruding part 34d are formed in a direction of an axis of the plunger 32. Among the two plunger side protruding parts, the plunger side first protruding part 34c is formed at two locations on the sides opposed to each other on the same outer circumference of the plunger 32 as shown in FIG. 11(b).

As shown in FIG. 11(a), the plunger stopper part 48 is composed of a plunger stopper 44 that is protruded inside from the inner circumferential face of the syringe barrel 20 and a cut part 46 that is formed on an inner circumference the same as that of the plunger stopper 44.

In the present embodiment, the plunger stopper 44 is formed at two locations on the sides opposed to each other on the same inner circumference of the syringe barrel 20 corresponding to the position of the plunger side first protruding part 34c in such a manner that a movement of the plunger 32 in a direction of an axis of the syringe barrel 20 is stopped in the case in which the plunger side first protruding part 34c is abutted to the plunger stopper 44.

Moreover, the cut part 46 is formed at two locations on the sides opposed to each other on the same inner circumference of the syringe barrel 20 corresponding to the position of the plunger side first protruding part 34c in such a manner that the plunger side first protruding part 34c can pass through the cut part 46.

The positions and the number of the plunger stoppers 44 and the cut parts 46 can be corresponded to the positions and the number of the plunger side first protruding parts 34c in such a manner that a movement of the plunger 32 in a direction of an axis of the syringe barrel 20 is stopped in the case in which the plunger side first protruding part 34c is abutted to the plunger stopper 44 and in such a manner that the plunger side first protruding part 34c can pass through the cut part 46. Under the above conditions, the positions and the number of the plunger stoppers 44 and the cut parts 46 can be modified as needed depending on an application of use.

A width L3 in a plunger outer circumferential direction of the plunger side first protruding part 34c is smaller than a width L4 in a syringe barrel inner circumferential direction of the cut part 46 in such a manner that the plunger side first protruding part 34c can pass through the cut part 46. In the present embodiment, the width L3 in a plunger outer circumferential direction of the plunger side first protruding part 34c is approximately ¼ of an outer circumferential length of the plunger 32.

Moreover, a distance L5 between the plunger side first protruding part 34c and the plunger side second protruding part 34d and a distance L6 between the syringe barrel side protruding part 25 and the plunger stopper part 48 are not restricted in particular. However, as shown in the present embodiment, it is preferable that the distance L5 is substantially equivalent to the distance L6 in such a manner that the plunger side first protruding part 34c is abutted to the plunger stopper 44 of the plunger stopper part 48 at the same time when the plunger side second protruding part 34d is abutted to the syringe barrel side protruding part 25 as described later.

For the prefilled type nasal drip appliance 10 that has been configured as described above, as shown in FIG. 12(a), in the state in which the plunger side first protruding part 34c is abutted to the syringe barrel side protruding part 25, a plunger rear end part 36 of the plunger 32 is pressed. In the case in which the plunger side first protruding part 34c of the plunger 32 gets over the syringe barrel side protruding part 25, the piston 30 presses the medicinal solution 50 by a pressing force that is applied to the plunger 32 at that time. Moreover, the medicinal solution 50 makes the center stopper 40 to get over the conduction part 24, the medicinal solution 50 then flows into the flow path 28 through the medical solution inflow groove 27, and the medicinal solution 50 is sprayed outside from the spray hole 21 (in the state of FIG. 12(b)).

Moreover, as shown in FIG. 12(c), the plunger side first protruding part 34c is abutted to the plunger stopper 44 of the plunger stopper part 48 at the same time when the plunger side second protruding part 34d is abutted to the syringe barrel side protruding part 25. At that time, a movement of the plunger 32 in a direction of an axis of the syringe barrel 20 is stopped, and a spray of the medicinal solution 50 is also stopped.

In this case, the plunger stopper 44 is configured in such a manner that the plunger side first protruding part 34c that has been abutted to the plunger stopper 44 cannot easily get over the plunger stopper 44 in order to stop a movement of the plunger 32 in a direction of an axis of the syringe barrel 20. In order to further move the plunger 32 in a direction of the spray hole of the syringe barrel 20, it is necessary to rotate the plunger 32 by a predetermined angle α. In the present embodiment, the plunger 32 is rotated by 90° as shown in FIG. 11(b).

In other words, by rotating the plunger 32 by 90° in the state of FIG. 11(b), the plunger side first protruding part 34c is located in the directions of three o'clock and nine o'clock in the figure similarly to the location of the cut part 46 shown in FIG. 11(a). In that case, since the width L3 in a plunger outer circumferential direction of the plunger side first protruding part 34c is smaller than the width L4 in a syringe barrel inner circumferential direction of the cut part 46, the plunger side first protruding part 34c can be located in such a manner that the plunger side first protruding part 34c can pass through the cut part 46 (in the state of FIG. 13(a)).

In the present embodiment, as a mark in the case in which the plunger 32 is rotated by a predetermined angle, a syringe barrel side identification mark 47 is formed on the syringe barrel 20, and a plunger side identification mark 49 is formed on the plunger 32, whereby the plunger 32 can be rotated by a predetermined angle with a certainty.

In the next place, as shown in FIG. 13(b), in the case in which the plunger rear end part 36 is pressed again and a pressure is applied to the plunger 32 in such a manner that the plunger side second protruding part 34b can get over the syringe barrel side protruding part 25, the remaining medicinal solution 50 is sprayed outside from the spray hole 21 similarly to the processes as described above.

As described above, in the present embodiment, the plunger side first protruding part 34c and the plunger stopper part 48 are configured in such a manner that it is necessary to rotate the plunger 32 by a predetermined angle α in order to further move the plunger 32 in a direction of a spray of the syringe barrel 20 in the case in which the plunger 32 is moved in a direction of the spray hole of the syringe barrel 20 and the plunger side first protruding part 34c is abutted to the plunger stopper 44. Consequently, in the case in which the spray of the medicinal solution 50 is carried out a plurality of times, the medicinal solution 50 of an amount for a plurality of times can be prevented from being sprayed at once in the wrong, and the medicinal solution 50 of an amount for once can be sprayed for every time with a certainty.

Similarly to the embodiment 2, the present embodiment has described an example in which the plunger side protruding part 34 is formed at two locations to enable the spray of two times. However, the present invention is not restricted to the embodiment. The number of the plunger side protruding parts 34 can be increased corresponding to the number of times of sprays, and the number of the plunger side protruding parts 34 can be selected properly as needed.

While the preferred embodiments in accordance with the present invention have been described above, the present invention is not restricted to the embodiments. For the prefilled type nasal drip appliance 10 in accordance with the present embodiment for instance, the syringe barrel side protruding part 25 is formed at the end part of the syringe barrel 20. However, the position of the syringe barrel side protruding part 25 is not restricted to the embodiment. Providing the plunger side protruding part 34 can get over the syringe barrel side protruding part 25, the syringe barrel side protruding part 25 can be formed at any position of the inner circumferential face of the syringe barrel 20, and the syringe barrel side protruding part 25 can be formed in any shape.

Moreover, for the center stopper 40 in accordance with the present embodiment, the shapes of an upper face and a lower face are in a planar state in parallel in a direction of an axis of the syringe barrel 20. However, the shapes of an upper face and a lower face are not restricted to the embodiment. For instance, the shapes of an upper face and a lower face can also be formed in such a manner that the upper face and the lower face are widespread outward. In the case of such a shape, the conduction part 24 should be formed in such a manner that the center stopper 40 can get over the conduction part 24 entirely and the medicinal solution 50 can be flown to the side of the spray hole 21.

As described above, the prefilled type nasal drip appliance in accordance with the present invention is not restricted to the embodiments, and various changes, modifications, and functional additions can be thus made without departing from the scope of the present invention.

The invention claimed is:

1. A prefilled type nasal drip appliance comprising:
   a syringe barrel provided with a spray hole of a medicinal solution on one side and a medical solution storage part that stores the medicinal solution in advance on the other side;
   an elastic piston that is inserted into the syringe barrel in a slidable manner to the inner circumferential face of the syringe barrel;
   a plunger that is attached to the rear end of the piston and that enables the piston to be moved in a direction of an axis of the syringe barrel; and
   an elastic center stopper that is inserted into the syringe barrel in such a manner that the center stopper is located between the spray hole and the piston and that can slide on the inner circumferential face of the syringe barrel,
   wherein the medicinal solution is stored between the center stopper and the piston in a liquid-tight state in advance,
   the syringe barrel is provided with a center stopper locking part between the spray hole formed on one side and the center stopper, a conduction part that is a passage way that can introduce the medicinal solution is formed at one location or a plurality of locations in the center stopper locking part,
   a syringe barrel side protruding part that is protruded inside from the inner circumferential face of the syringe barrel is formed on the other end side of the syringe barrel,
   the plunger is provided with a plunger side protruding part that is protruded outside from the outer circumferential face of the plunger is formed at a generally central part in a direction of an axis of the plunger,
   the syringe barrel side protruding part and the plunger side protruding part are configured to be engaged with each other and the engagement is configured to be released with a pressure of a predetermined level or more when the plunger is moved in a direction of the spray hole of the syringe barrel and the plunger side protruding part gets over the syringe barrel side protruding part,
   a pressure of a predetermined level or more is applied to the plunger, the plunger is moved in a direction of the spray hole of the syringe barrel, the engagement of the plunger side protruding part and the syringe barrel side protruding part is released,
   the medicinal solution moves the center stopper in a direction of the spray hole by the pressure that is applied to the plunger in the release of the engagement,
   the center stopper gets over the conduction part that is formed to the center stopper locking part, a medical solution inflow groove is formed between the conduction part and the center stopper, the medical solution storage part and the spray hole are interconnected with each other, and
   the medicinal solution is therefore flown and moved in a direction of the spray hole from the medical solution inflow groove, whereby the medicinal solution can be sprayed from the spray hole.

2. The prefilled type nasal drip appliance as defined in claim 1, wherein the conduction part that is formed to the center stopper locking part is formed in the range at least equivalent to a thickness width in a direction of an axis of the center stopper that is moved in a direction of an axis of the syringe barrel or in the range equivalent to or larger than a width of a contact part of the center stopper that comes into contact with the syringe barrel.

3. The prefilled type nasal drip appliance as defined in claim 1, wherein the plunger side protruding part that is formed on the plunger is formed at one location or a plurality of locations in a direction of an axis of the plunger.

4. The prefilled type nasal drip appliance as defined in claim 1, wherein:
   the plunger side protruding part that is formed on the plunger is formed at a plurality of locations in a direction of an axis of the plunger,
   the syringe barrel is provided with the plunger stopper part that includes; a plunger stopper that is protruded inside from the inner circumferential face of the syringe barrel and that stops a movement of the plunger in a direction of an axis of the syringe barrel in the case in which the plunger side protruding part is abutted to the plunger stopper; and a cut part that is formed on an inner circumference the same as that of the plunger stopper and that enables the plunger side protruding part to pass through the cut part, and the plunger side protruding part and the plunger stopper part are configured in such a manner that the plunger is required to be rotated by a predetermined angle in order to move further the plunger in a direction of a spray for the syringe barrel in the case in which the plunger is moved in a direction of the spray hole of the syringe barrel and the plunger side protruding part is abutted to the plunger stopper, whereby the spray of a plurality of times can be carried out.

5. The prefilled type nasal drip appliance as defined in claim 1, wherein a finger applying part in a flange shape that is protruded outside from the outer circumferential face of the syringe barrel is formed at a generally central position in a direction of an axis of the syringe barrel.

6. The prefilled type nasal drip appliance as defined in claim 1, wherein the syringe barrel is formed by a molding in an integrated manner.

7. The prefilled type nasal drip appliance as defined in claim 1, wherein the plunger that is attached to the piston is configured in a detachable manner to the piston.

8. The prefilled type nasal drip appliance as defined in claim 1, wherein a material of the syringe barrel is a cyclic olefin series resin.

9. The prefilled type nasal drip appliance as defined in claim 1, wherein a tetrafluoroethylene film is laminated on the surface of the piston and the center stopper.

10. The prefilled type nasal drip appliance as defined in claim 2, wherein the plunger side protruding part that is formed on the plunger is formed at one location or a plurality of locations in a direction of an axis of the plunger.

11. The prefilled type nasal drip appliance as defined in claim 2, wherein:

the plunger side protruding part that is formed on the plunger is formed at a plurality of locations in a direction of an axis of the plunger, the syringe barrel is provided with the plunger stopper part that includes; a plunger stopper that is protruded inside from the inner circumferential face of the syringe barrel and that stops a movement of the plunger in a direction of an axis of the syringe barrel in the case in which the plunger side protruding part is abutted to the plunger stopper; and a cut part that is formed on an inner circumference the same as that of the plunger stopper and that enables the plunger side protruding part to pass through the cut part, and the plunger side protruding part and the plunger stopper part are configured in such a manner that the plunger is required to be rotated by a predetermined angle in order to move further the plunger in a direction of a spray for the syringe barrel in the case in which the plunger is moved in a direction of the spray hole of the syringe barrel and the plunger side protruding part is abutted to the plunger stopper, whereby the spray of a plurality of times can be carried out.

12. The prefilled type nasal drip appliance as defined in claim 2, wherein a finger applying part in a flange shape that is protruded outside from the outer circumferential face of the syringe barrel is formed at a generally central position in a direction of an axis of the syringe barrel.

13. The prefilled type nasal drip appliance as defined in claim 2, wherein the syringe barrel is formed by a molding in an integrated manner.

14. The prefilled type nasal drip appliance as defined in claim 2, wherein the plunger that is attached to the piston is configured in a detachable manner to the piston.

15. The prefilled type nasal drip appliance as defined in claim 2, wherein a material of the syringe barrel is a cyclic olefin series resin.

16. The prefilled type nasal drip appliance as defined in claim 2, wherein a tetrafluoroethylene film is laminated on the surface of the piston and the center stopper.

* * * * *